US011850017B2

(12) United States Patent
Pflaumer et al.

(10) Patent No.: US 11,850,017 B2
(45) Date of Patent: *Dec. 26, 2023

(54) SERVICE LIFE MANAGEMENT FOR AN INSTRUMENT OF A ROBOTIC SURGERY SYSTEM

(71) Applicant: Titan Medical Inc., Toronto (CA)

(72) Inventors: Hans Christian Pflaumer, Raleigh, NC (US); Aki Hannu Einari Laakso, Raleigh, NC (US); Perry A. Genova, Chapel Hill, NC (US)

(73) Assignee: Titan Medical Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/066,971

(22) Filed: Dec. 15, 2022

(65) Prior Publication Data
US 2023/0120627 A1  Apr. 20, 2023

Related U.S. Application Data

(63) Continuation of application No. 17/152,033, filed on Jan. 19, 2021, now Pat. No. 11,529,207.

(51) Int. Cl.
*G09G 5/00* (2006.01)
*A61B 34/00* (2016.01)

(52) U.S. Cl.
CPC .............. *A61B 34/74* (2016.02); *A61B 34/76* (2016.02)

(58) Field of Classification Search
CPC . G06T 2207/10061; G06T 2207/20084; G06T 7/11; H01J 2237/2803;
(Continued)

(56) References Cited

U.S. PATENT DOCUMENTS

2009/0248037 A1 10/2009 Prisco
2017/0071693 A1* 3/2017 Taylor .................... B25J 9/0009
(Continued)

FOREIGN PATENT DOCUMENTS

WO    WO 2022/159229    7/2022

OTHER PUBLICATIONS

International Search Report and Written Opinion received in PCT Application No. PCT/US2021/064633, dated Jun. 23, 2022.

*Primary Examiner* — Insa Sadio
(74) *Attorney, Agent, or Firm* — Knobbe, Martens, Olson & Bear, LLP

(57) ABSTRACT

A robotic surgery system is disclosed that can include an instrument including an operational tool coupled to a positioner and an input device configured to generate input signals in response to manipulation by an operator representing a desired spatial positioning of the tool within a tool workspace including extents corresponding to physical movement limitations for the positioner. A processor can be configured to receive the input signals and process the signals to determine the desired spatial positioning. The processor can be configured to initiate a movement management function in response to a determination that the desired spatial positioning would result in a movement of the positioner associated with a potential service life reduction for the instrument. The processor can be configured to generate drive signals for movement of the positioner in response to a determination that the desired spatial positioning is not associated with a potential reduction in service life.

21 Claims, 11 Drawing Sheets

(58) Field of Classification Search
CPC ............ H01J 2237/2809; H01J 37/222; H01J 37/265; H01J 37/28; G01N 2223/401; G01N 2223/408; G01N 2223/418; G01N 23/2251; A61B 34/74; A61B 34/76
See application file for complete search history.

(56) References Cited

U.S. PATENT DOCUMENTS

2018/0360550 A1* 12/2018 Nakanishi .............. A61B 34/70
2020/0337790 A1  10/2020 Mumaw et al.

* cited by examiner

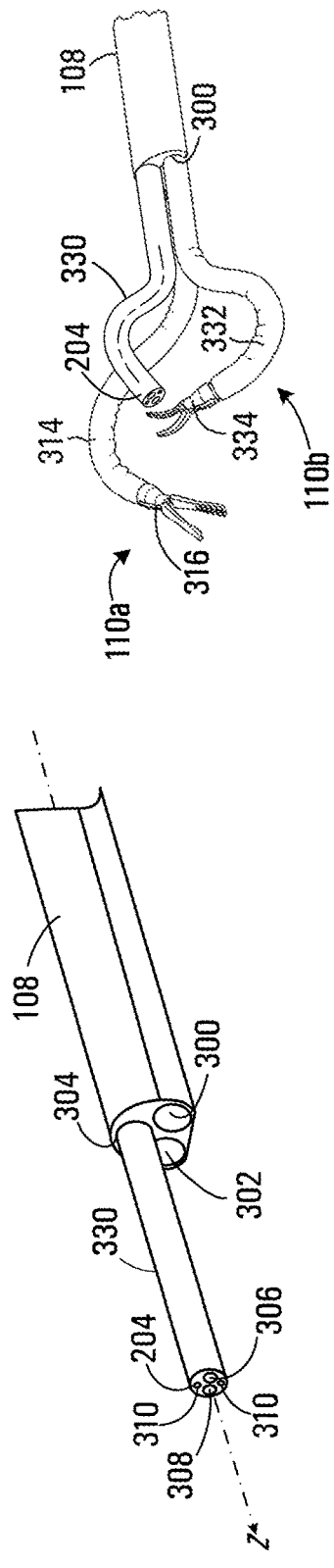
FIG. 3A
FIG. 3C
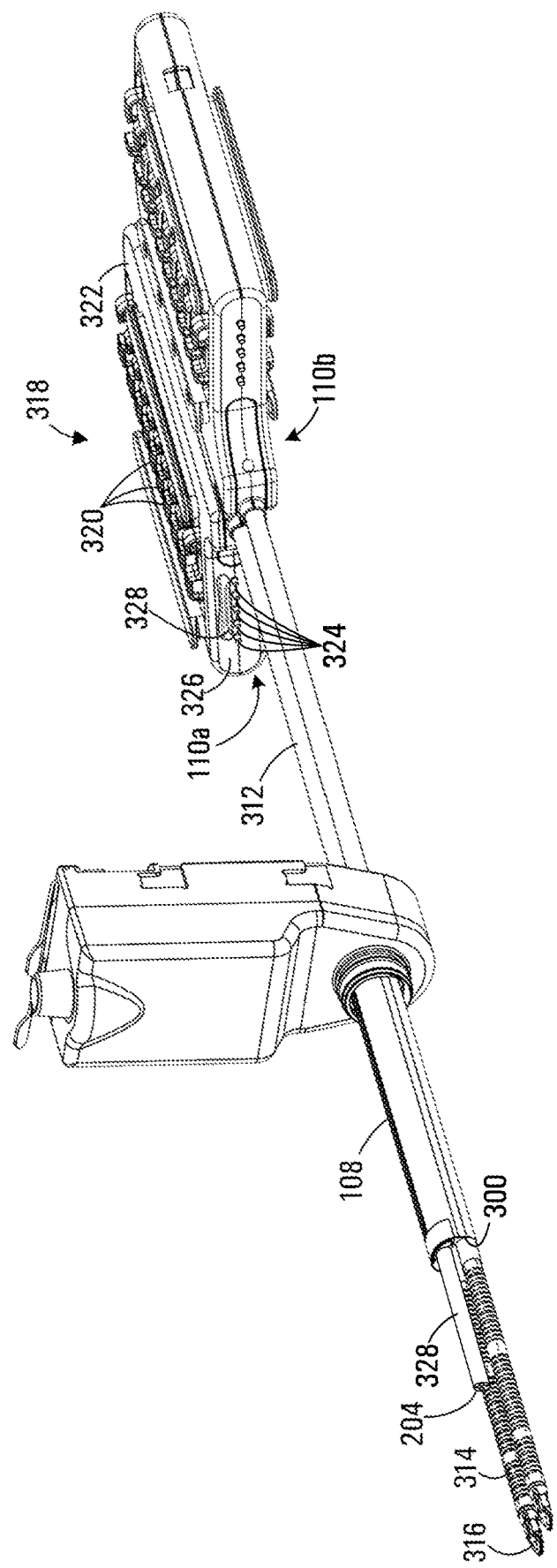
FIG. 3B

SERVICE LIFE MANAGEMENT FOR AN INSTRUMENT OF A ROBOTIC SURGERY SYSTEM

BACKGROUND

1. Field

This disclosure relates generally to a surgical instrument apparatus for performing a surgical procedure within a body cavity of a patient.

2. Description of Related Art

Surgical instruments used in laparoscopic and/or robotic surgery generally have a service life that is pre-determined based on testing or estimated based on material and structural properties of the instrument. The service life may be expressed as a total number of uses or a total usage time. Alternatively, the service life may be based on actual usage parameters such as the number of movements or discrete operations, for example. Use of the instrument beyond the pre-determined service life is considered to be associated with decreased performance and/or increased risk of failure of the instrument.

SUMMARY

In accordance with one disclosed aspect there is provided a robotic surgery system. The system may include an input device configured to generate input signals in response to manipulation by an operator, the input signals representing a desired spatial positioning of a tool of an instrument within a tool workspace, the tool workspace including extents corresponding to physical movement limitations associated with a positioner of the instrument to which the tool is coupled. The system may include a processor configured to receive the input signals from the input device and process the input signals to determine the desired spatial positioning of the tool within the tool workspace. The processor may be configured to, in response to a determination that the desired spatial positioning would result in a movement of the positioner associated with a potential service life reduction for the instrument, initiate a movement management function. The processor may be configured to, in response to a determination that the desired spatial positioning would not result in the movement of the positioner associated with the potential service life reduction for the instrument, generate drive signals for movement of the positioner to cause the tool to be positioned at a position corresponding to the desired spatial positioning in the tool workspace.

The processor may be configured to make the determination that the desired spatial positioning would result in the movement of the positioner associated with the potential service life reduction by determining that the desired spatial positioning associated with the input signals lies outside a pre-determined safe region of the tool workspace.

The processor may be configured to initiate the movement management function by temporarily permitting the operator to extend the pre-determined safe region to permit the tool to move outside the pre-determined safe region.

The input device may be configured to deliver a haptic feedback to an operator of the input device and the processor may be configured to generate the alert by causing the input device to deliver the haptic feedback.

The processor may be configured to initiate the movement management function by causing an alert to be generated to indicate to the operator that the desired movement is associated with the potential service life reduction, and generating drive signals to inhibit movement of the positioner to cause the tool to remain positioned at a current position in tool workspace.

The processor may be configured to initiate the movement management function by causing an alert to be generated to indicate to the operator that the desired spatial positioning is associated with the potential service life reduction, and in response to receiving an override input from the operator, generate drive signals for movement of the positioner to cause the tool to be positioned at the position in the tool workspace, and update a service life parameter associated with the instrument based on an expected reduction in service life caused by the movement.

The service life parameter may include a pre-determined number of uses for the instrument, the number of uses being decremented each time the instrument is used in a surgical procedure, and the processor may be configured to decrement the number of uses based on the expected reduction in service life caused by the movement.

The service life parameter may include a pre-determined usage time and the processor may be configured to decrement the usage time based on the expected reduction in service life caused by the movement.

The service life parameter may include a pre-determined number of movements of the positioner that are associated with the potential service life reduction, and the processor may be configured to decrement the number of movements each time the override input is received from the operator.

The processor may be configured to discontinue generating drive signals for movements of the positioner that are associated with the potential service life reduction responsive to expiry of an override period.

The system may include a display configured to display an image of the tool workspace to the operator and the processor may be configured to cause the alert to be generated by causing displaying of an alert icon on the display.

The processor may be configured to cause displaying an interactive alert icon on the display, the interactive alert icon being configured to generate the override input when activated by the operator.

The input device may be configured to deliver a haptic feedback to an operator of the input device and the processor may be configured to causing the input device to deliver the haptic feedback.

The service life parameter may be stored in a memory associated with the instrument, and the processor may be configured to update the service life parameter by writing a new service life parameter to the memory.

The memory may include a memory located on the instrument, and the system may include an instrument interface configured to place the processor in data communication with the memory responsive to the instrument being loaded into the system.

Access for reading and writing to the memory may be protected by a security function to prevent unauthorized changes to the service life parameter.

The memory may include a memory of the processor and the service life parameter may include an identifier that associates the service life parameter with the instrument.

The positioner may include a plurality of articulated linkages, and a plurality of control wires that are pushed or pulled to cause movement of the articulated linkages to position the tool within the tool workspace, and the determination that the desired spatial positioning would result in the movement of the positioner associated with the potential service life reduction may be based on an estimated strain in the control wires associated with the movement.

The tool may include an end effector positioned at a distal end of the tool and the end effector may include a pair of opposing elements, the opposing elements being actuated to close by an end effector actuation signal received from the input device, and the processor may be configured to determine an end effector drive signal for causing the opposing elements to close with a desired force in proportion to the end effector actuation signal, and in response to a determination that the desired force would result in the potential service life reduction for the instrument, initiate an actuation management function, and in response to a determination that the desired force would not result in the potential service life reduction for the instrument, generate the end effector drive signal to cause the end effector to close with the desired force.

There is provided a method of operating a robotic surgery system of any of the preceding paragraphs and/or disclosed below.

In accordance with another disclosed aspect there is provided a method for operating a robotic surgery system, the robotic surgery system including a processor and an input device. The method may be implemented by the processor. The method may involve receiving input signals in response to manipulation of the input device by an operator, the input signals representing a desired spatial positioning of a tool of an instrument within a tool workspace, the tool workspace including extents corresponding to physical movement limitations associated with a positioner of the instrument to which the tool is coupled. The method may involve processing the input signals to determine the desired spatial positioning of the tool within the tool workspace. The method may involve, in response to a determination that the desired spatial positioning would result in a movement of the positioner associated with a potential service life reduction for the instrument, initiating a movement management function. The method may involve, in response to a determination that the desired spatial positioning would not result in a movement of the positioner associated with the potential service life reduction, generating drive signals for movement of the positioner to cause the tool to be positioned at a position corresponding to the desired spatial positioning in the tool workspace.

Initiating the movement management function may involve generating an alert to indicate to the operator that the desired spatial positioning is associated with the potential service life reduction, and in response to receiving an override input from the operator, generating drive signals for movement of the positioner to cause the tool to be positioned at the position in the tool workspace, and updating a service life parameter associated with the instrument based on an expected reduction in service life caused by the movement.

Other aspects and features will become apparent to those ordinarily skilled in the art upon review of the following description of specific disclosed embodiments in conjunction with the accompanying figures.

BRIEF DESCRIPTION OF THE DRAWINGS

In drawings which illustrate disclosed embodiments,

FIG. 3A is a perspective view of a portion of an insertion tube associated with the drive unit shown in FIGS. 2A and 2B;

FIG. 3B is a perspective view of the insertion tube with a pair of instruments inserted;

FIG. 3C is a perspective view of a portion of the insertion tube with the instruments shown in a deployed state;

DETAILED DESCRIPTION

Figure 1:
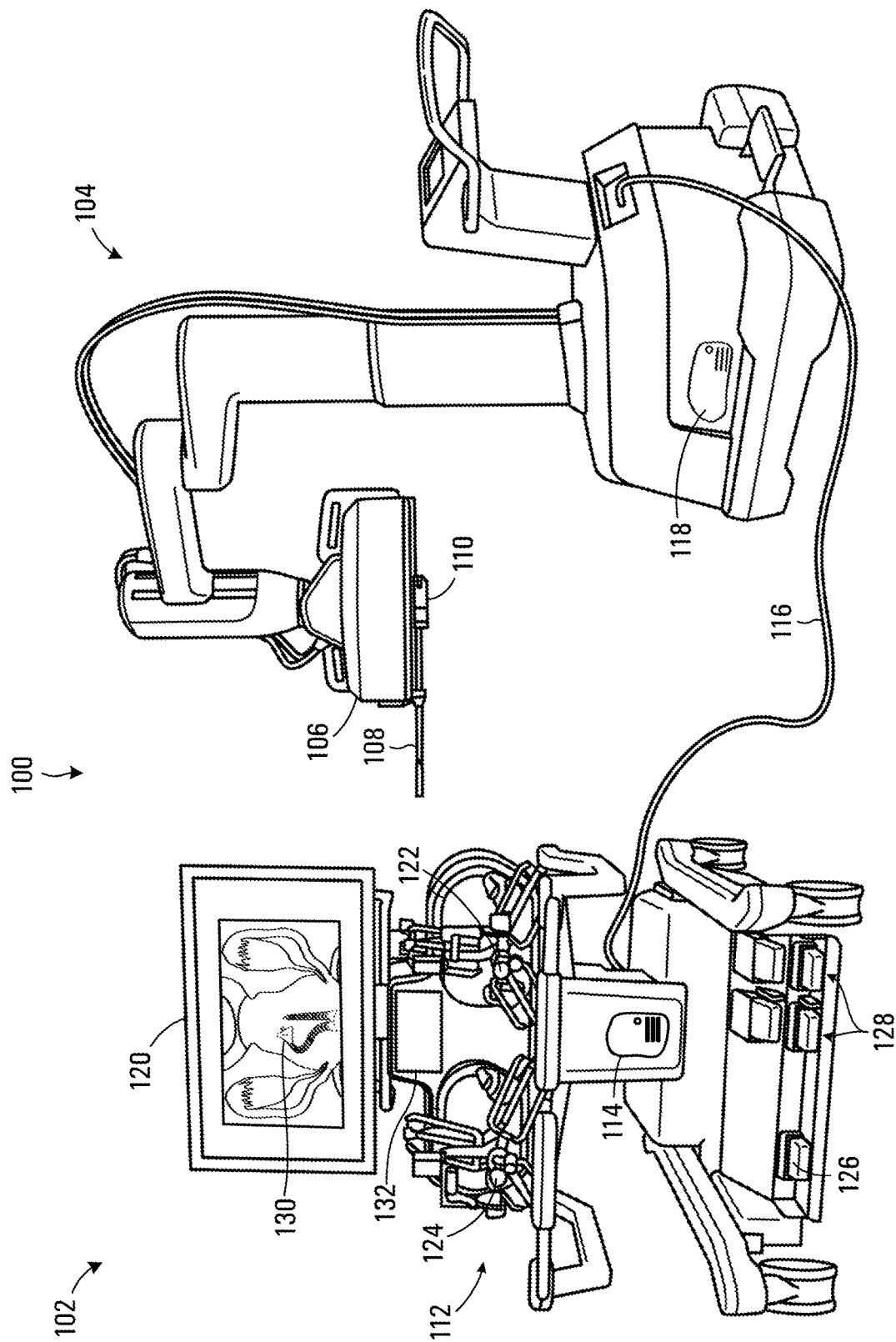
FIG. 1 is a perspective view of a robotic surgery system in accordance with one disclosed embodiment.

Referring to FIG. 1, a robotic surgery system in accordance with one disclosed embodiment is shown generally at 100. The system 100 includes a workstation 102 and an instrument cart 104. The instrument cart 104 includes a drive unit 106 to which an insertion tube 108 and an instrument 110 are mounted. The workstation 102 includes an input device 112 that receives operator input and produces input signals. The input device 112 may also be capable of generating haptic feedback to the operator. The input device 112 may be implemented using a haptic interface available from Force Dimension, of Switzerland, for example.

In the embodiment shown, the workstation 102 further includes a workstation processor circuit 114 in communication with the input device 112 for receiving the input signals and generating drive signals for controlling the robotic surgery system, which are transmitted to the instrument cart 104 via an interface cable 116. The input device 112 includes right and left hand controllers 122 and 124, which are grasped by the operator's hands and moved to cause the input device 112 to produce the input signals. The workstation 102 also includes a footswitch 126 for generating an enablement signal. The workstation 102 may also include other footswitches 128 that provide an additional input to the system as described below. The workstation 102 also includes a display 120 in communication with the workstation processor circuit 114.

The display 120 may be configured for displaying images of the surgical workspace and portions of the instruments 110 that are within the surgical workspace. In the embodiment shown, the workstation 102 further includes a secondary display 132 for displaying status information related to the system 100. The instrument cart 104 includes an instrument processor circuit 118 that receives and the input signals from the workstation processor circuit 114 and produces drive signals operable to drive the instrument 110 during a surgical procedure.

Figure 2A:
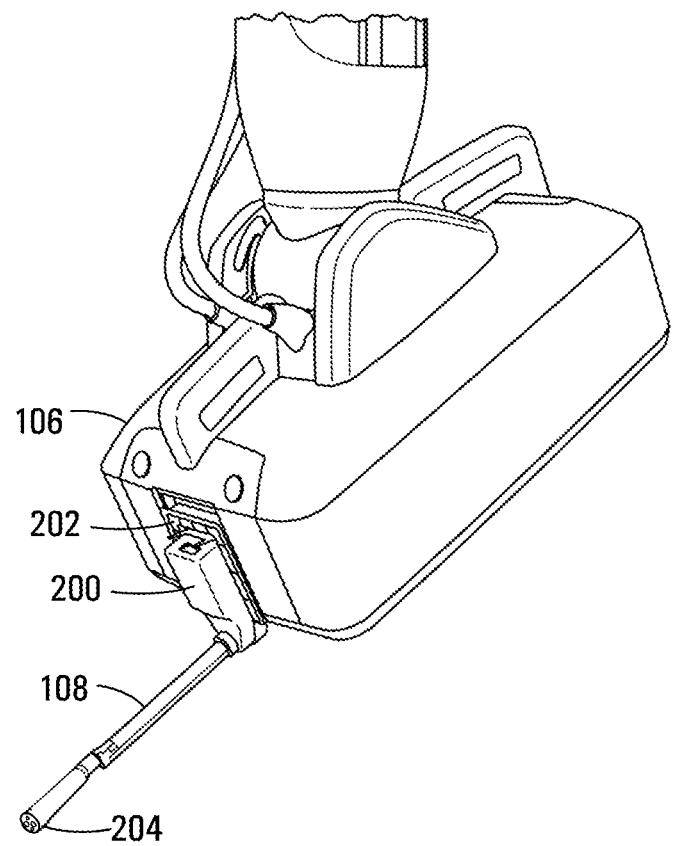
FIG. 2A is a front perspective view of a drive unit of the system shown in FIG. 1.
Figure 2B:
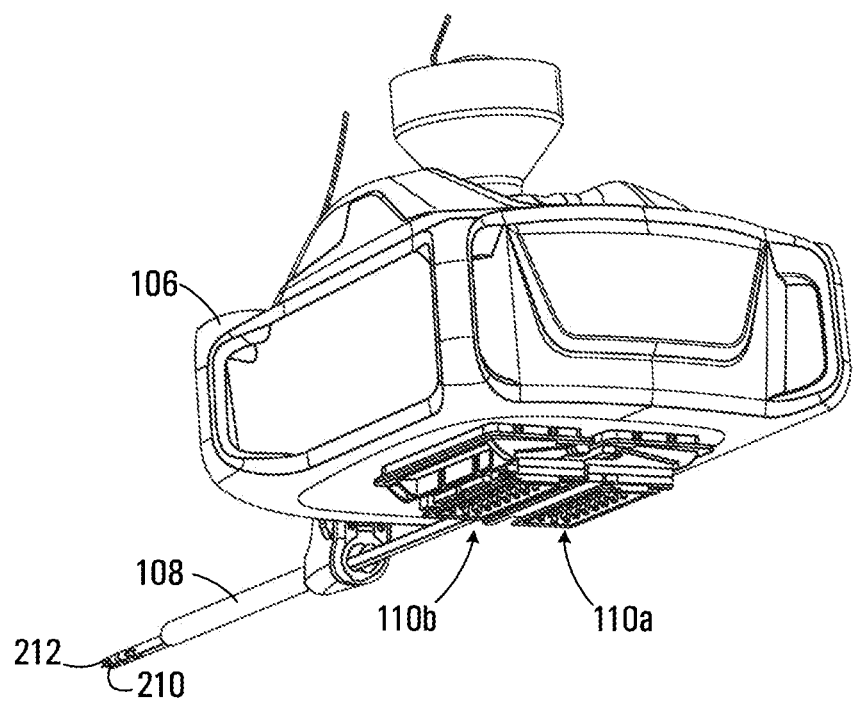
FIG. 2B is a rear perspective view of the drive unit of the system shown in FIG. 1.

The drive unit 106 is shown in isolation in FIGS. 2A and 2B. Referring to FIG. 2A, the insertion tube 108 includes a drive interface 200 that detachably mounts to a corresponding drive interface 202 on the drive unit 106. The insertion tube 108 includes a camera 204 at a distal end of the insertion tube, which is inserted into a body cavity of a patient to capture body cavity image data representing an interior view of the body cavity for display on the display 120 of the workstation 102. Referring to FIG. 2B, in this embodiment the insertion tube 108 includes a pair of adjacent bores extending through the insertion tube for receiving a right hand side instrument 110*a* and a left hand side instrument 110*b*. The instruments 110*a* and 110*b* each include a respective operational tool 210 and 212 at a distal end. The operational tools 210 and 210 may be one of a variety of different operational tools, such as a probe, dissector, hook, or cauterizing tool. As an example, the operational tools 210 and 210 may be configured as an end effector having opposing jaws that provide an actuated function such as a scissor for cutting tissue or forceps for gripping tissue. In other embodiments one of the instruments 110*a* or 110*b* may include an operational tool 210 or 212 in the form of a distally located camera that provides imaging functions in addition to or in place of the camera 204. One of the instruments 110*a* or 110*b* may include an operational tool in the form of an illuminator configured to provide illumination for generation of images by the camera 204.

A portion of the insertion tube 108 is shown in FIG. 3A and includes two adjacently located bores 300 and 302 extending through the insertion tube 108 for receiving the respective surgical instruments 110*a* and 110*b*. The insertion tube 108 also includes a third bore 304 for receiving the camera 204. In alternative embodiments, the camera 204 may be fixedly mounted to a distal portion of the insertion tube 108. The camera 204 is configured as a stereoscopic camera having a pair of spaced apart imagers 306 and 308 for producing stereoscopic views representing an interior view of the body cavity. The camera 204 also includes an integrated illuminator 310 for illuminating the body cavity for capturing images. The integrated illuminator 310 may be implemented using an illumination source such as a light emitting diode or an illumination source may be remotely located and may deliver the illumination through an optical fiber running through the insertion tube 108.

Referring to FIG. 3B, the instruments 110*a* and 110*b* are shown inserted through the respective bores 300 and 302 of the insertion tube 108 (in FIG. 3B the bore 302 is not visible and the drive unit 106 has been omitted for sake of illustration). The right hand side instrument 110*a* includes a rigid shaft portion 312 and a positioner portion 314 that extends outwardly from the bore 300. In this embodiment the instrument 110*a* includes an end effector 316 that acts as the operational tool 210. The positioner 314 may include an articulated tool positioner as described in detail in commonly owned PCT patent publication WO2014/201538 entitled "ARTICULATED TOOL POSITIONER AND SYSTEM EMPLOYING SAME" filed on Dec. 20, 2013 and incorporated herein by reference in its entirety. The described positioner in PCT patent publication WO2014/201538 provides for dexterous movement of the end effector 316 through a plurality of articulated segments.

In this embodiment, the instrument 110*a* includes an actuator 318 including a plurality of actuator slides 320 disposed in a housing 322. The housing 322 is located at a proximal end of the instrument 110*a* that couples to a corresponding interface (not shown) on the drive unit 106 for moving the positioner 314 and actuating the end effector 316. The actuator 318 of the instrument 110*a* may be generally configured as disclosed in commonly owned PCT patent publication WO2016/090459 entitled "ACTUATOR AND DRIVE FOR MANIPULATING A TOOL" filed on Feb. 18, 2015 and incorporated herein by reference in its entirety. The interface of the drive unit 106 may have a track system (not shown) coupled to the actuator 318 for longitudinally advancing and retracting the instrument 110*a* to cause the rigid shaft portion 312 to move within the bore 300. The longitudinal positioning of the instrument 110*a* places the end effector 316 at a desired longitudinal offset with respect to the insertion tube 108 for accessing a surgical workspace within the body cavity of the patient.

The instrument 110*a* also includes a plurality of electrical contact pins 324 disposed on a forward facing portion 326 of the actuator housing 322. The pins 324 are in communication with an instrument usage monitor board 328, which is shown in cut away view located within the actuator housing 322. The pins 324 are disposed to engage and electrically connect to similar pins (not shown) disposed on the drive unit 106 for placing the monitor board 328 into communication with the instrument processor circuit 118. As an example, the pins 324 may be implemented using sprung pogo connector pins. The instrument 110*b* is shown in FIG. 3B in side-by side relation and identically configured to the instrument 110*a*. In some embodiments, the instrument 110*b* may have a different operational tool 212 than the instrument 110*a*.

The camera 204 is mounted on an articulated arm 330 moveable in response to drive forces delivered by the drive interface 202 of the drive unit 106 to the drive interface 200 of the insertion tube 108. Drive forces delivered by the drive unit 106 cause the camera 204 to move from the longitudinally extended insertion state shown in FIG. 3A and 3B to a deployed state as shown in FIG. 3C.

Drive forces are imparted on the plurality of actuator slides 320 of the actuator 318 by the drive unit 106, which causes the positioner 314 of the instrument 110 to perform dexterous movement to position the end effector 316 for performing various surgical tasks. As shown in FIG. 3C, the left instrument 110*b* is also shown along with an associated positioner 332 and an end effector 334. In the deployed position shown in FIG. 3C, the camera 204 is able to generate images of the body cavity without obstructing movements of the positioners 314 and 332.

Figure 4:
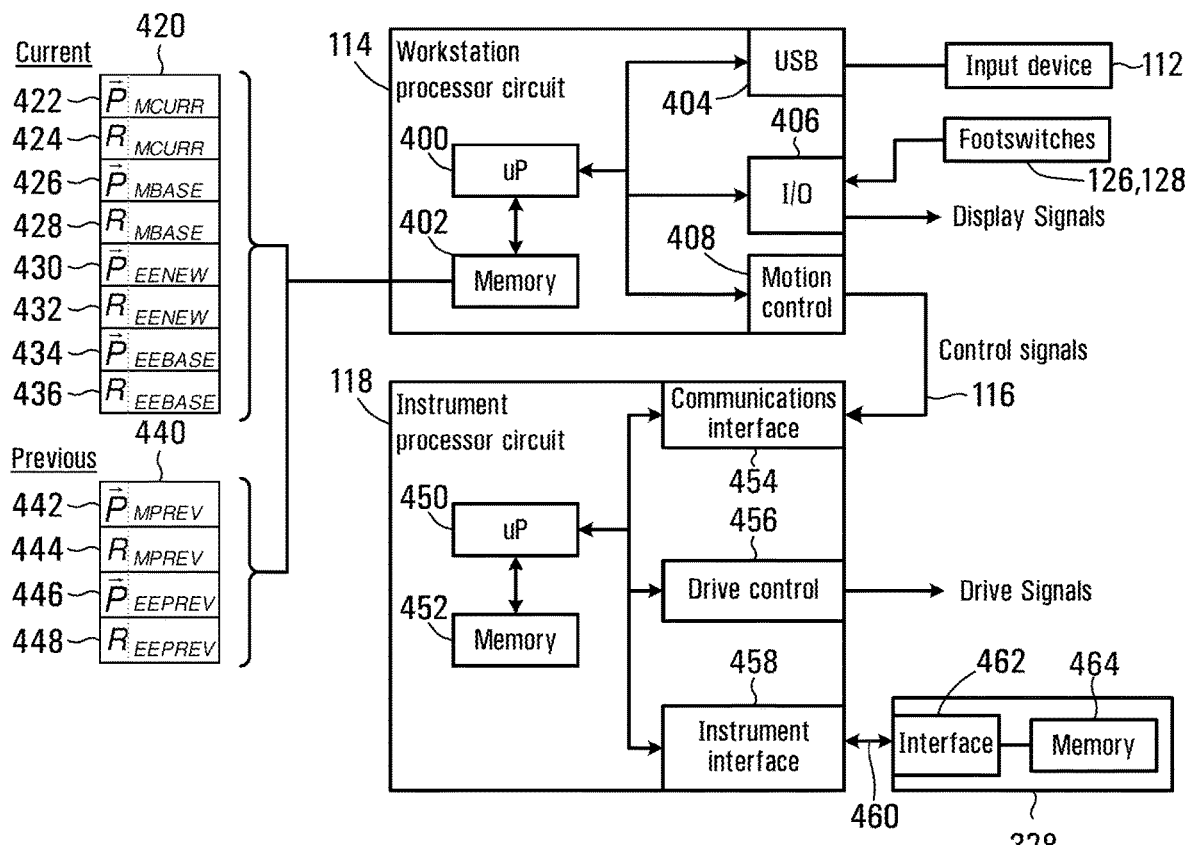
FIG. 4 is a block diagram of processor circuit elements of the system shown in FIG. 1.

A block diagram of the processor circuit elements of the system 100 is shown in FIG. 4. Referring to FIG. 4 the workstation processor circuit 114 includes a microprocessor 400. The workstation processor circuit 114 also includes a workstation memory 402, a USB interface 404, an input/output 406 and a motion control interface 408, all of which are in communication with the microprocessor 400. The input/output 406 includes an input for receiving the enablement signal from the footswitches 126 and 128 and an output for producing display signals for driving the display 120. In this embodiment the input device 112 communicates using a USB protocol and the USB interface 404 receives input signals produced by the input device in response to movements of the hand controllers 122 and 124. The workstation memory 402 includes a current buffer 420 and a previous buffer 440 including a plurality of stores for storing values associated with the control signals, as described later herein.

The instrument processor circuit 118 includes a microprocessor 450, a memory 452, a communications interface 454, and a drive control interface 456, all of which are in communication with the microprocessor.

The microprocessor 450 receives the control signals at the communications interface 454 based on the input signals received at the workstation processor circuit 114. The microprocessor 450 processes the control signals and causes the drive control interface 456 to produce drive signals for moving the instruments 110a and 110b.

The workstation processor circuit 114 thus acts as a controller subsystem for receiving user input, while the instrument processor circuit 118 acts as a responder subsystem in responding to the user input and driving the instruments 110a and 110b. While the embodiment shown includes the workstation processor circuit 114 and the instrument processor circuit 118, in other embodiments a single processor circuit may be used to perform both controller and responder functions.

In the embodiment shown, the instrument processor circuit 118 further includes an instrument data interface 458 having signal lines 460 that connect via the pins 324 on the instrument actuator 318 to the monitor board 328. In one embodiment the instrument data interface 458 may be implemented as a universal asynchronous receiver-transmitter (UART) or an PC (Inter-Integrated Circuit) interface. Alternatively the interface 458 may be implemented using an interface such as Synchronous Serial Interface (SSI), Serial Peripheral Interface Bus (SPI), EtherCAT (Ethernet for Control Automation Technology), or a Controller Area Network (CAN bus), for example. The monitor board 328 includes an interface 462 and a memory 464. The memory 464 may be a persistent memory such as a NOR or NAND flash memory or other type of persistent memory. The interface 462 on the monitor board 328 facilitates writing data received via instrument interface 458 to the memory 464 or reading out data from the memory 464. In some embodiments the interface 462 may implement security protocols to prevent unauthorized access to the memory 464.

Figure 5:
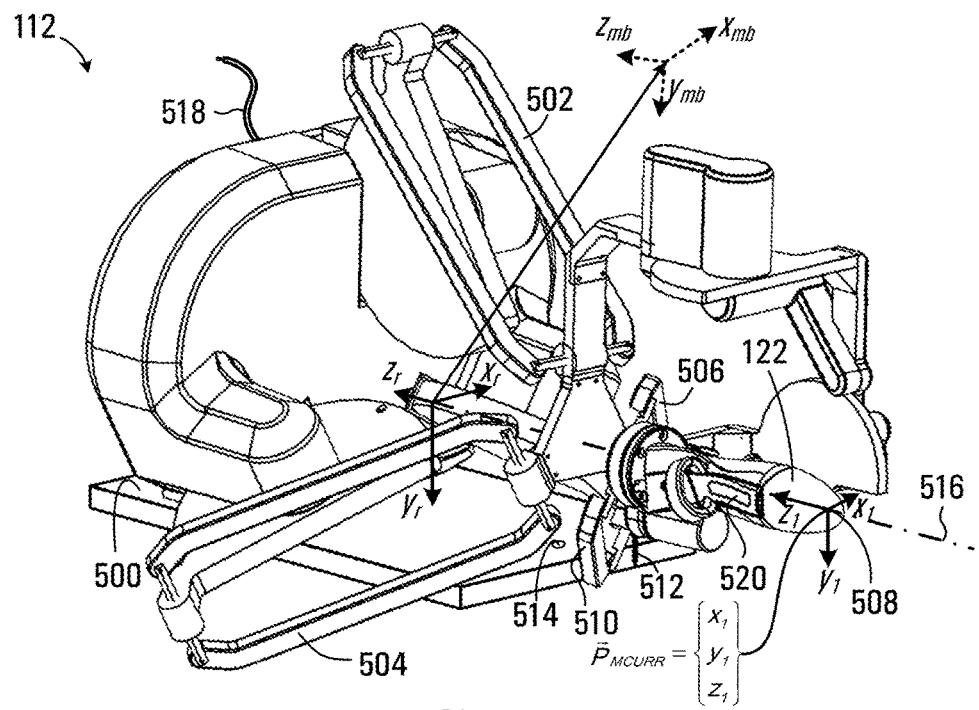
FIG. 5 is a right hand controller portion of an input device of the system shown in FIG. 1.

A portion of the input device 112 that includes the right hand controller 122 is shown in greater detail in FIG. 5. For simplicity, only the right hand controller 122 of the input device 112 will be further described, it being understood that the left hand controller 124 operates in the same way. The input device 112 is supported on a base 500 and includes arms 502, 504, and 506 that provide a mounting for the hand controller 122, which may be grasped by the operator and moved within an input device workspace. The arms 502-506 permit positioning and rotation about orthogonal axes $x_1$, $y_1$, and $z_1$ of a Cartesian reference frame defining the input workspace. The Cartesian reference frame has an origin at a point on a body of the hand controller 122 and the location of the origin defines the hand controller position 508 (i.e. at the origin). In this embodiment, the hand controller 122 is mounted on a gimbal mount 510. The arms 502-506 confine movements of the hand controller 122 and hence the hand controller position 508 to within a generally hemispherical input device workspace. In one embodiment the input device 112 may also be configured to generate haptic forces for providing haptic feedback to the hand controller 122 through the arms 502-506 and gimbal mount 510. The hand controller 122 also includes an end effector actuator 520 that may be opened and closed to actuate movement of an end effector as described in more detail later herein.

The input device 112 includes sensors (not shown) that sense the position of each of the arms 502-506 and rotation of the hand controller 122 about each of the $x_1$, $y_1$, and $z_1$ axes and produces signals representing the position of the hand controller in the input device workspace and the rotational orientation of hand controller relative to an input device Cartesian reference frame $x_r$, $y_r$, $z_r$. In this embodiment, the position and orientation signals are transmitted as input signals via the USB connection 518 to the USB interface 404 of the workstation processor circuit 114.

In this embodiment, the gimbal mount 510 has a pin 512 extending downwardly from the mount and the base 500 includes a calibration opening 514 for receiving the pin. When the pin 512 is received in the opening 514 the hand controller 122 is located in a calibration position that is defined relative to the input device Cartesian reference frame $x_r$, $y_r$, $z_r$. The input device reference frame has an $x_r$-$z_r$ plane parallel to the base 500 and a $y_r$ axis perpendicular to the base. The $z_r$ axis is parallel to the base 500 and is coincident with an axis 516 passing centrally through the hand controller 122.

The input device 112 produces current hand controller signals and current hand controller orientation signals that represent the current position and orientation of the hand controller 122. The signals may be represented by a current hand controller position vector and a current hand controller rotation matrix. The current hand controller position vector is given by:

$$\vec{P}_{MCURR} = \begin{Bmatrix} x_1 \\ y_1 \\ z_1 \end{Bmatrix},$$

where $x_1$, $y_1$, and $z_1$ represent coordinates of the hand controller position 508 (i.e. the origin of the coordinate system $x_1$, $y_1$, $z_1$) relative to the input device reference frame $x_r$, $y_r$, $z_r$. The current hand controller rotation matrix is given by:

$$R_{MCURR} = \begin{bmatrix} x_{1x} & y_{1x} & z_{1x} \\ x_{1y} & y_{1y} & z_{1y} \\ x_{1z} & y_{1z} & z_{1z} \end{bmatrix},$$

where the columns of the matrix represent the axes of the hand controller reference frame $x_1$, $y_1$, $z_1$ relative to the input device reference frame $x_r$, $y_r$, $z_r$. The matrix $R_{MCURR}$ thus defines the current rotational orientation of the hand controller 122 relative to the $x_r$, $y_r$, and $z_r$ fixed controller reference frame. The current hand controller position vector $\vec{P}_{MCURR}$ and current handle rotation matrix $R_{MCURR}$ are transmitted as current hand controller position and current hand controller orientation signals via the USB connection 518 to the USB interface 404 of the workstation processor circuit 114. The workstation processor circuit 114 stores the three values representing the current handle position vector $\vec{P}_{MCURR}$ in a store 422 and the nine values representing the current hand controller rotation matrix $R_{MCURR}$ in a store 424 of the current buffer 420 of workstation memory 402.

Figure 6:
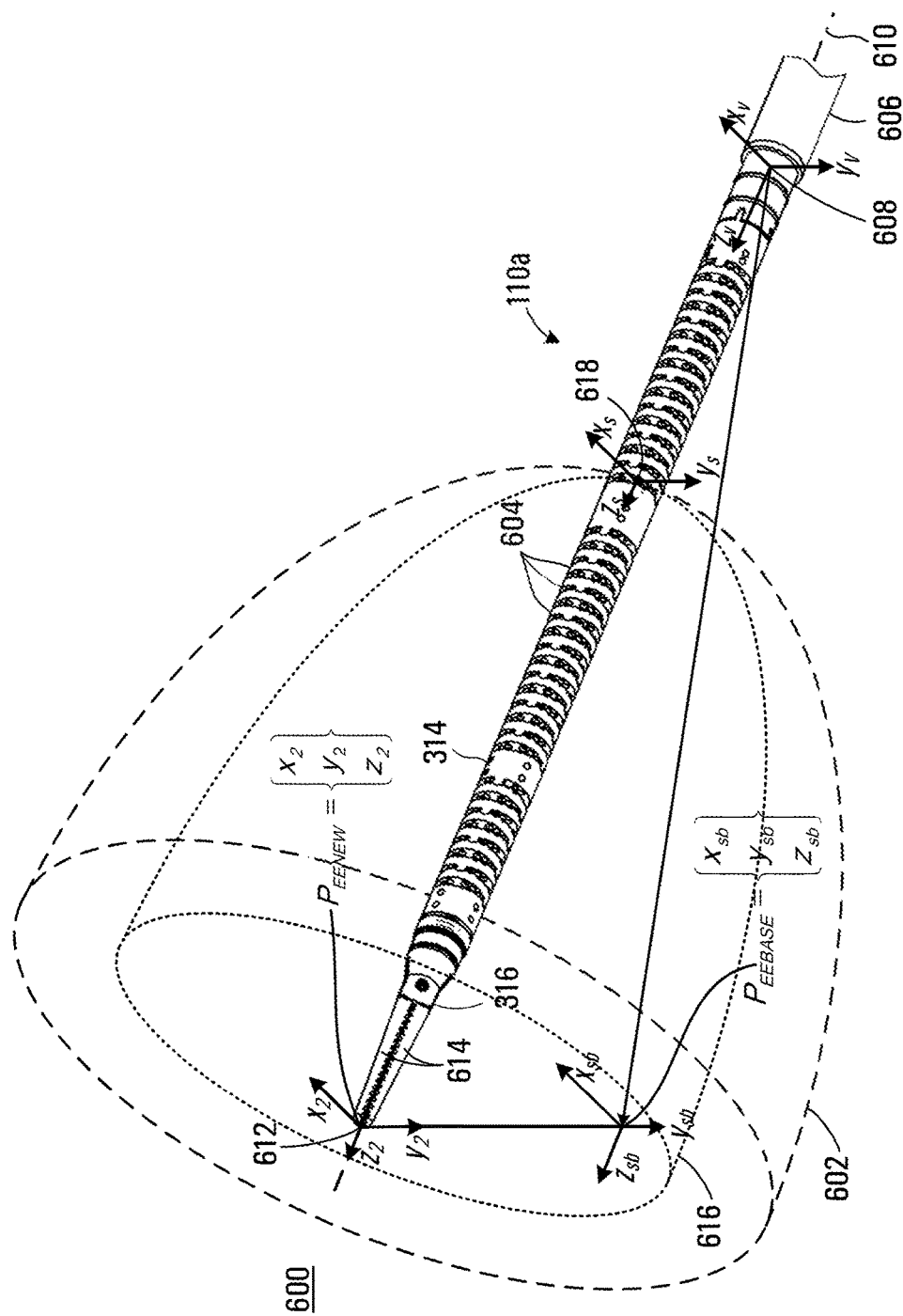
FIG. 6 is a detailed perspective view of the right side instrument shown in FIG. 3B.

The right side instrument 110a is shown in greater detail in FIG. 6. Referring to FIG. 6, the positioner 314 of the instrument 110a operates within a surgical workspace 600. The positioner 314 of the instrument 110a is configured to position the end effector 316 within a tool workspace 602 indicated by the broken lines in FIG. 6. The surgical workspace 600 will generally be larger than the tool workspace 602 since the tool may be longitudinally advanced or retracted to access different portions of the surgical workspace. The instrument cart 104 may also be repositioned to facilitate access to different portions of the surgical workspace 600. The microprocessor 400 of the workstation processor circuit 114 processes the input signals based on a current mapping between the input device workspace for the input device 112 and the surgical workspace 600 and causes the motion control interface 408 to transmit control signals, which are conveyed to the instrument processor circuit 118 via the interface cable 116. The mapping may include a scale factor that scales movements in input device workspace to produce scaled movements in surgical workspace 600. For example, a 100 mm translation in input device workspace may be scaled by a scale factor of 0.5 to produce a 50 mm movement in surgical workspace 600 for fine movement.

The positioner 314 positions the end effector 316 within the tool workspace 602 by activating various drivers in the drive unit 106 in response to the drive signals produced by the drive control interface 456 of the instrument processor circuit 118. The drivers in the drive unit 106 are coupled to deliver actuation forces to the plurality of actuator slides 320 of the actuator 318. The drive signals are produced by the drive control interface 456 in response to the control signals received at the communications interface 454 from the workstation processor circuit 114 and are based on the current hand controller position vector $\vec{P}_{MCURR}$ and current hand controller rotation matrix $R_{MCURR}$ stored in the stores 422 and 424 of the current buffer 420 in the workstation memory 402.

In this embodiment the positioner 314 of the instrument 110a includes a plurality of the identical "vertebra" 604 as described in commonly owned PCT patent application PCT/CA2013/001076 entitled "ARTICULATED TOOL POSITIONER AND SYSTEM EMPLOYING SAME" filed on Dec. 20, 2013, which is incorporated herein by reference in its entirety. The vertebra 604 are operable to move with respect to each other when control wires passing through the vertebra are extended or retracted to cause movements of the positioner 314. The control wires are coupled to the actuator slides 320, which when moved by the drive unit 106 position the end effector 316 within the surgical workspace 600. The position and orientation of the end effector 316 is defined relative to a fixed responder reference frame having axes $x_v$, $y_v$, and $z_v$, which intersect at a point referred to as the fixed responder reference position 608. The fixed responder reference position 608 lies on a longitudinal axis 610 of the instrument 110a and is contained in a plane perpendicular to the longitudinal axis and containing a distal edge of the insertion tube 606. In one embodiment the fixed responder reference frame acts as a body cavity frame of reference.

In the embodiment shown, the end effector 316 includes opposing gripper jaws 614 that are positioned and oriented within an end effector workspace. A tip of the gripper jaws 614 may be designated as an end effector position 612 defined as the origin of an end effector Cartesian reference frame $x_2$, $y_2$, $z_2$. The end effector position 612 is defined relative to the responder reference position 608 and the end effector may be positioned and orientated relative to the fixed responder reference frame $x_v$, $y_v$, $z_v$ for causing movement of the positioner 314 and/or the end effector 316.

The current hand controller position signal $\vec{P}_{MCURR}$ and current hand controller orientation signal $R_{MCURR}$ cause movement of the end effector 316 of the instrument 110a to new end effector positions and desired new end effector orientations represented by a new end effector position vector $\vec{P}_{EENEW}$:

$$\vec{P}_{EENEW} = \begin{Bmatrix} x_2 \\ y_2 \\ z_2 \end{Bmatrix},$$

where $x_2$, $y_2$, and $z_2$ represent coordinates of the end effector position 612 within the end effector workspace relative to the $x_v$, $y_v$, $z_v$ fixed responder reference frame. The new end effector orientation is represented by a 3×3 end effector rotation matrix $R_{EENEW}$:

$$R_{EENEW} = \begin{bmatrix} x_{2x} & y_{2x} & z_{2x} \\ x_{2y} & y_{2y} & z_{2y} \\ x_{2z} & y_{2z} & z_{2z} \end{bmatrix},$$

where the columns of the $R_{EENEW}$ matrix represent the axes of the end effector reference frame $x_2$, $y_2$, and $z_2$ written in the fixed responder reference frame $x_v$, $y_v$, and $z_v$. The rotation matrix $R_{EENEW}$ thus defines a new orientation of the end effector 316 in the end effector workspace, relative to the $x_v$, $y_v$, and $z_v$ fixed responder reference frame. Values for the vector $\vec{P}_{EENEW}$ and rotation matrix $R_{EENEW}$ are calculated as described later herein and stored in stores 430 and 432 of the current buffer 420 of the workstation memory 402 respectively.

When the system 100 initially starts up, the workstation processor circuit 114 sets a controller base position vector $\vec{P}_{MBASE}$ equal to the current hand controller vector $\vec{P}_{MCURR}$ and causes a definable controller base rotation matrix $R_{MBASE}$ to define an orientation that is the same as the current orientation defined by the hand controller rotation matrix $R_{MCURR}$ associated with the current hand controller rotation. At startup, the following operations are therefore performed:

$$\vec{P}_{MBASE} = \vec{P}_{MCURR}, \text{ and}$$

$$R_{MBASE} = R_{MCURR}.$$

For the example of the instrument 110a, the hand controller 122 reference frame represented by the axes $x_1$, $y_1$, and $z_1$ shown in FIG. 5 and the definable controller base reference frame represented by the axes $m_{ob}$, $y_{mb}$, and $z_{mb}$ (also shown in FIG. 5) thus coincide at startup of the system 100. Referring back to FIG. 4, the workstation processor circuit 114 stores the values representing the definable controller base position vector $\vec{P}_{MBASE}$ and the definable controller base rotation matrix $R_{MBASE}$ in the stores 426 and 428 of the current buffer 420 of the workstation memory 402.

At startup of the system 100 there would be no previously stored values for the new end effector position vector $\vec{P}_{EENEW}$ and the new end effector rotation matrix $R_{EENEW}$ and in one embodiment these values are set to home configuration values. A home configuration may be defined that produces a generally straight positioner 314 for the instrument 110a as shown in FIG. 6 and the values of $\vec{P}_{EENEW}$ and $R_{EENEW}$ for the home configuration may be preconfigured at initialization. On startup of the system 100 the workstation processor circuit 114 also causes a definable end effector base position vector $\vec{P}_{EEBASE}$ and a definable end effector base rotation matrix $R_{EEBASE}$ to be set to the home configuration values of $\vec{P}_{EENEW}$ and $R_{EENEW}$. Additionally, values for $\vec{P}_{EEPREV}$ and $R_{EEPREV}$ stored in the stores 446 and 448 of the previous buffer 440 (shown in FIG. 4) of the workstation processor circuit 114 are also set to the home configuration values of $\vec{P}_{EENEW}$ and $R_{EENEW}$. In other embodiments, the home configuration may define configuration variables to produce different bent or both straight and bent positioning device poses for the home configuration. At startup, the following operations are therefore performed:

$$\vec{P}_{EEBASE} = \vec{P}_{EENEW} = \vec{P}_{EEPREV}, \text{ and}$$

$$R_{EEBASE} = R_{EENEW} = R_{EEPREV}.$$

The end effector reference frame represented by the axes $x_2$, $y_2$, and $z_2$ shown in FIG. 6 and the definable responder base reference frame represented by the axes $x_{sb}$, $y_{sb}$, and $z_{sb}$ thus coincide at startup of the system 100. Referring back to FIG. 4, the workstation processor circuit 114 stores the values $x_{sb}$, $y_{sb}$, and $z_{sb}$ representing the definable responder base position vector $\vec{P}_{EEBASE}$ in store 434 and stores the values representing the definable responder base rotation matrix $R_{MBASE}$ in a store 436 of the current buffer 420 of the workstation memory 402.

The tool workspace 602 lies within the surgical workspace 600, and in this embodiment is represented by an elliptic paraboloid surface in the reference frame $x_v$, $y_v$, $z_v$, which is given by:

$$\frac{x^2}{a^2} + \frac{y^2}{b^2} = \frac{z}{c}.$$

For the instrument 110a, since the positioner 314 is capable of symmetrical movements in any direction, the parameters a and b are equal. In other embodiments the instrument 110 may be configured to provide non-symmetrical movements in different directions and thus the parameters a and b may differ. The parameter c offsets the paraboloid with respect to the fixed responder reference position 608 to a position 618 defined by the axes $x_s$, $y_s$, $z_s$, since physical limitations due to the vertebra 604 would prohibit movement close to the reference position 608. In other embodiments the tool workspace 602 may be defined by a surface other than the elliptic paraboloid shown in FIG. 6 or by a look up table of coordinates that may be interpolated to define a continuous 602.

In FIG. 6, a second elliptic paraboloid surface 616 is shown lying within the tool workspace 602 and represents a pre-determined safe region within the tool workspace 602. In one embodiment, movements within the safe region 616 are considered to not cause a potential service life reduction for the instrument 110a. Movements beyond the safe region, but still within the tool workspace 602, are associated with an increased mechanical stress being placed on the components of the instrument 110a. In this embodiment a safe region 616 is defined having the same shape as the tool workspace 602. However, in other embodiments, the safe region 616 may have a different surface shape.

Figure 7:
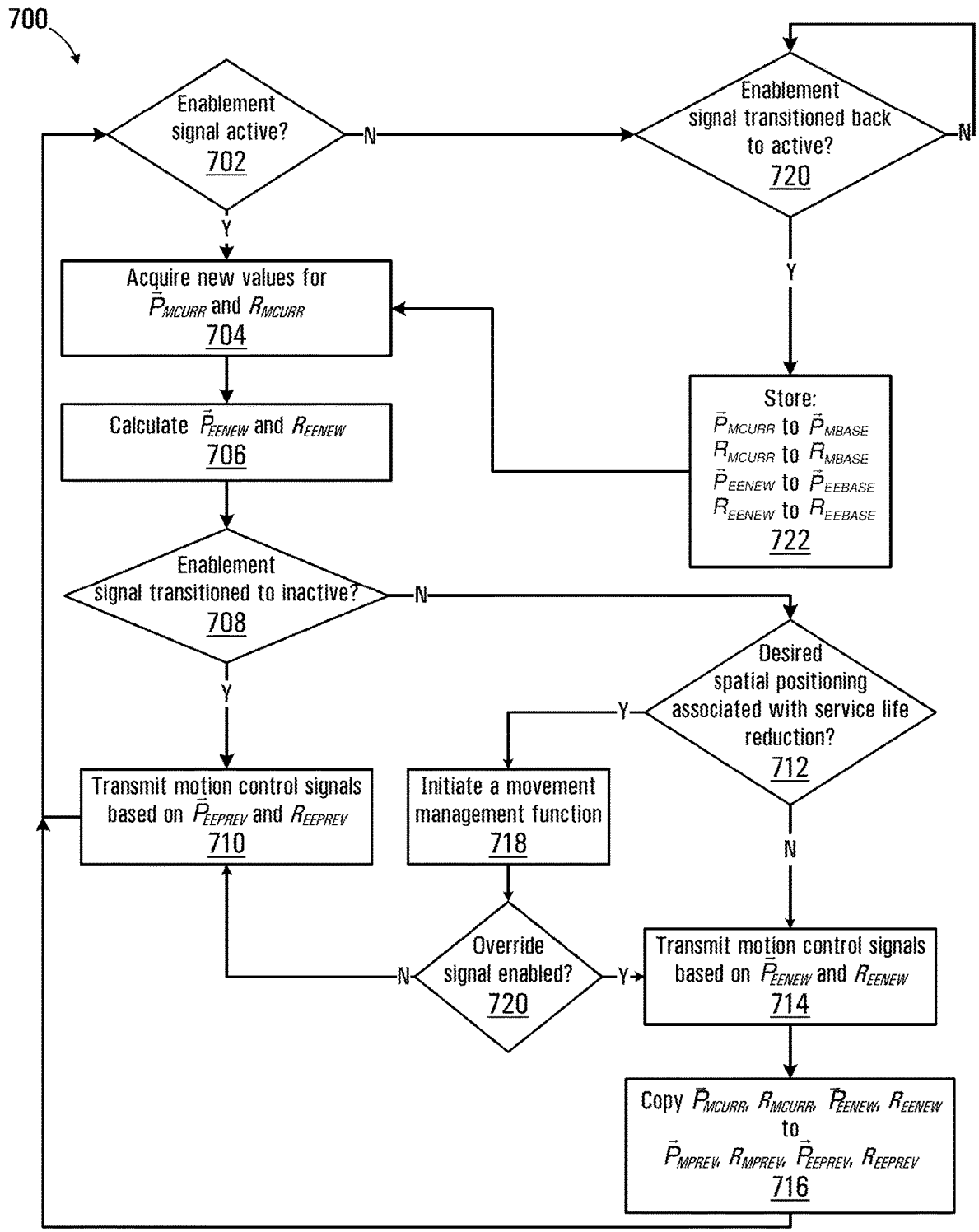
FIG. 7 is a flowchart of a movement process implemented by the workstation processor circuit shown in FIG. 4.

Referring to FIG. 7, a flowchart depicting blocks of code for directing the workstation processor circuit 114 to execute a process for moving the instrument 110a is shown generally at 700. The blocks generally represent codes that direct the microprocessor 400 to perform various functions. The actual code to implement each block may be written in any suitable program language, such as C, C++, C#, Java, OpenGL, and/or assembly code, for example.

The movement process 700 begins at block 702, which directs the microprocessor 400 to determine whether the enablement signal generated by the footswitch 126 is in an active state. If at block 702, it is determined that the footswitch 126 is currently released, the enablement signal will be in the active state and the microprocessor is directed to block 704, which directs the microprocessor 400 to read new values for $\vec{P}_{MCURR}$ and $R_{MCURR}$ from the current buffer 420 of the workstation memory 402, which represent the current hand controller position vector $\vec{P}_{MCURR}$ and current hand controller matrix $R_{MCURR}$. Block 706 then directs the microprocessor 400 to calculate new end effector position signals $\vec{P}_{EENEW}$ and new end effector orientation signals $R_{EENEW}$ representing a desired end effector position 612 and desired end effector orientation, relative to the fixed responder reference position 608 and the responder base orientation (shown in FIG. 6). Block 706 also directs the microprocessor 400 to store values representing the new end effector position vector $\vec{P}_{EENEW}$ in the store 430 and to store values representing the desired end effector orientation matrix $R_{EENEW}$ in the store 432 of the current buffer 420 of the workstation memory 402.

The new end effector position signals $\vec{P}_{EENEW}$ and new end effector orientation signals $R_{EENEW}$ are calculated according to the following relations:

$$\vec{P}_{EENEW} = A(\vec{P}_{MCURR} - \vec{P}_{MBASE}) + \vec{P}_{EEBASE} \qquad \text{Eqn 1a}$$

$$R_{EENEW} = R_{EEBASE} R_{MBASE}^{-1} R_{MCURR} \qquad \text{Eqn 1b}$$

where:

$\vec{P}_{EENEW}$ is the new end effector position vector that represents the new desired position of the end effector 316 in the end effector workspace, and is defined relative to the responder base reference position;

A is a scalar value representing a scaling factor in translational motion between the hand controller 122 (controller) and the instrument 110a (responder);

$\vec{P}_{MCURR}$ is the current representation of the hand controller position vector stored in the store 422 of the current buffer 420, the hand controller position vector being defined relative to the fixed controller reference frame $x_r$, $y_r$, and $z_r$;

$\vec{P}_{MBASE}$ is the last-saved position vector $\vec{P}_{MCURR}$ for the hand controller 122 that was shifted at the last transition of the enablement signal from the inactive state to the active state or on system initialization or by operation of a control interface by an operator;

$\vec{P}_{EEBASE}$ is the last saved position vector $\vec{P}_{EENEW}$ for the end effector 316 that was shifted at the last transition of the enablement signal from the inactive state to the active state or on system initialization;

$R_{EENEW}$ is the new end effector orientation matrix representing the current orientation of the end effector 316, and is defined relative to the fixed responder reference position 608;

$R_{EEBASE}$ is the last-saved rotation matrix $R_{EENEW}$ of the end effector 316 shifted at the last transition of the enablement signal from the inactive state to the active state;

$R_{MBASE}^{-1}$ is the inverse of rotation matrix $R_{MBASE}$, which is the last-saved rotation matrix $R_{MCURR}$ of the hand controller 122 saved at the last transition of the enablement signal from the inactive state to the active state; and $R_{MCURR}$ is the currently acquired rotation matrix representing the orientation of hand controller 122 relative to the fixed controller reference frame $x_r$, $y_r$, and $z_r$.

Block 708 then directs the microprocessor 400 to determine whether the enablement signal has transitioned to the inactive state. If the enablement signal has transitioned to the inactive state, the microprocessor 400 is directed to block 710. Block 710 directs the microprocessor 400 to cause the motion control interface 408 to transmit control signals based on the previously calculated values of $\vec{P}_{EEPREV}$ and $R_{EEPREV}$ in the respective stores 446 and 448 of the previous butter 440 of the workstation memory 402. The control signals transmitted by the motion control interface 408 are thus derived from the last saved values of $\vec{P}_{EENEW}$ and $R_{EENEW}$. The instrument processor circuit 118 receives the control signals and produces drive signals at the drive control interface 456 that inhibit further movement of the positioner 314 of the instrument 110a.

If the enablement signal has not transitioned to the inactive state at block 708, the microprocessor 400 is directed to block 712. Block 712 directs the microprocessor 400 to determine whether the desired spatial positioning of the positioner 314 of the instrument 110a would result in a movement of the positioner associated with a potential service life reduction for the instrument 110a. If at block 712, the spatial positioning of the positioner 314 is determined not to be associated with a potential service life reduction, then the microprocessor 400 is directed to block 714. Block 714 directs the microprocessor 400 to cause the motion control interface 408 to transmit control signals based on the newly calculated values for $\vec{P}_{EENEW}$ and $R_{EENEW}$. When the control signals are received at the communications interface 454 of the instrument processor circuit 118, the microprocessor 450 causes drive signals to be produced to cause the end effector 316 to assume a position and orientation in tool workspace determined by the current position and current orientation of the hand controller 122.

The process then continues at block 716, which directs the microprocessor 400 to copy the current position vector $\vec{P}_{MCURR}$ and the current rotation matrix $R_{MCURR}$ stored in stores 422 and 424 of the current buffer 420 into stores 442 ($\vec{P}_{MPREV}$) and 444 ($R_{MPREV}$) of the previous buffer 440 of the workstation memory 402. Block 716 also directs the microprocessor 400 to copy the newly calculated end effector position vector $\vec{P}_{EENEW}$ and the newly calculated end effector rotation matrix $R_{EENEW}$ into stores 446 and 448 of the previous buffer 440. By storing the newly calculated end effector position vector $\vec{P}_{EENEW}$ and newly calculated end effector rotation matrix $R_{EENEW}$, as previously calculated end effector position vector $\vec{P}_{EEPREV}$ and previously calculated end effector rotation matrix $R_{EEPREV}$, a subsequently acquired new end effector position vector $\vec{P}_{EENEW}$ and subsequently acquired new end effector rotation matrix $R_{EENEW}$ can be calculated from the next received hand controller position vector $\vec{P}_{MCURR}$ and next received hand controller rotation matrix $R_{MCURR}$ provided by the hand controller 122. Block 716 then directs the microprocessor 400 back to block 702, and the process is repeated.

If at block 712, the microprocessor 400 determines that the desired spatial positioning of the positioner 314 of the instrument 110a would result in a movement of the positioner associated with a potential service life reduction for the instrument 110a, the microprocessor is directed to block 718. Block 718 directs the microprocessor 400 to initiate a movement management function. The movement management function may include various steps, such as the generation of an alert and/or receiving an operator override and generating a corresponding override signal. Various process embodiments of the movement management function are described in more detail below.

When the movement management function block 718 has been initiated, the microprocessor 400 is directed to block 720, which directs the microprocessor 400 to determine whether an override signal has been enabled or asserted at block 718. If the microprocessor 400 determines that an operator override was received at block 720, the microprocessor 400 is directed to block 714, and the motion control signals based $\vec{P}_{EENEW}$ and rotation matrix $R_{EENEW}$ are transmitted as described above and the movements of the positioner 314 are permitted to proceed outside the safe region 616 of the tool workspace 602. If the microprocessor 400 determines that an override is not in effect at block 720, the microprocessor 400 is directed to block 710, and the motion control signals based $\vec{P}_{EEPREV}$ and rotation matrix $R_{EEPREV}$ are transmitted as described above and the end effector 316 is constrained within the safe region 616 of the tool workspace 602. In this case, the drive signals inhibit movement of the positioner 314 beyond the safe region 616 and cause the end effector 316 to remain positioned at a current position in the tool workspace 602. Further movements that would result in the end effector 316 remaining within the safe region 616 would however be permitted.

If at block 702, it is determined that the footswitch 126 is currently depressed, the enablement signal will be in the inactive state and the microprocessor is directed to block 720 initiating a base setting process. The base setting process is associated with blocks 720 and 722 and is executed asynchronously whenever the enablement signal produced by the footswitch 126 transitions from the active state to the inactive state. During the base setting process, the drive signals are maintained at the values that were in effect at the time the enablement signal transitioned to inactive at block 708. At block 720 the microprocessor 400 is directed to determine whether the enablement signal has transitioned back to being in the active state. While enablement signal remains inactive (i.e. while the footswitch 126 is depressed) the control signals transmitted by the motion control interface 408 are based only on the previously calculated end effector position and previously calculated orientation signals $\vec{P}_{EEPREV}$ and $R_{EEPREV}$ that were in effect before the enablement signal transitioned to inactive. If at block 720 the enablement signal remains in the inactive state, the microprocessor 400 is directed to repeat block 720 and the process is thus effectively suspended while the enablement signal remains in the inactive state. While the footswitch 126 is depressed, the surgeon may thus move the hand controller 122 to a new location to relocate the input device workspace relative to the surgical workspace 600.

When at block 720 the enablement signal transitions from the inactive state to the active state, the microprocessor 400 is directed to block 722. Block 722 directs the microprocessor 400 to set new base positions and orientations for the hand controller 122 and end effector 316 respectively. Block 722 directs the microprocessor 400 to cause current values of current hand controller position vector $\vec{P}_{MCURR}$ and the hand controller rotation matrix $R_{MCURR}$ to be written to stores 426 and 428 of the current buffer 420 workstation memory 402 as new values for the controller base position vector $\vec{P}_{MBASE}$ and controller base rotation matrix $R_{MBASE}$. Block 722 also directs the microprocessor 400 to cause current values for the end effector position signal $\vec{P}_{EENEW}$ and the end effector orientation signal $R_{EENEW}$ to be stored in stores 434 and 436 of the current buffer 420 as the definable end effector base position vector $\vec{P}_{EEBASE}$ and definable responder base rotation matrix $R_{MBASE}$. Following execution of block 722, the microprocessor 400 is directed back to block 704 of the process 700, which directs the microprocessor to permit further movement of the positioner 314 of the instrument 110a. The control signals transmitted by the motion control interface 408 thus cause the instrument processor circuit 118 to produce drive signals at the drive control interface 456 that cause further movement of the instrument 110a.

The base setting process implemented at blocks 720 and 722 thus allows the positioner 314 of the instrument 110a to be immobilized by depressing the footswitch 126 while the hand controller 122 of the input device 112 is moved to a new location. When the footswitch 126 is released, control of the positioner 314 of the instrument 110a resumes at the new position of the hand controller 122. The hand controller 122 may thus be repositioned as desired while the positioner 314 remains immobile, allowing a greater workspace to be accessed by the operator and preventing unintended movements that may inflict injury to the patient.

The end effector position vector $\vec{P}_{EENEW}$ or $\vec{P}_{EEPREV}$ and end effector orientation matrix $R_{EENEW}$ or $R_{EEPREV}$ produced at block 706 provides a desired location end effector tip 612 (shown in FIG. 6) with respect to the fixed reference position 608. In the processor embodiment shown in FIG. 4, the microprocessor 400 of the workstation processor circuit 114 causes the motion control interface 408 to transmit motion control signals that define a pose required by the positioner 314 to position and orient the end effector 316 in the desired end effector position and orientation. The motion control signals are thus generated based on a kinematic configuration of the positioner 314 and end effector 316 to place the end effector position 612 at a desired position and orientation.

Figure 8:
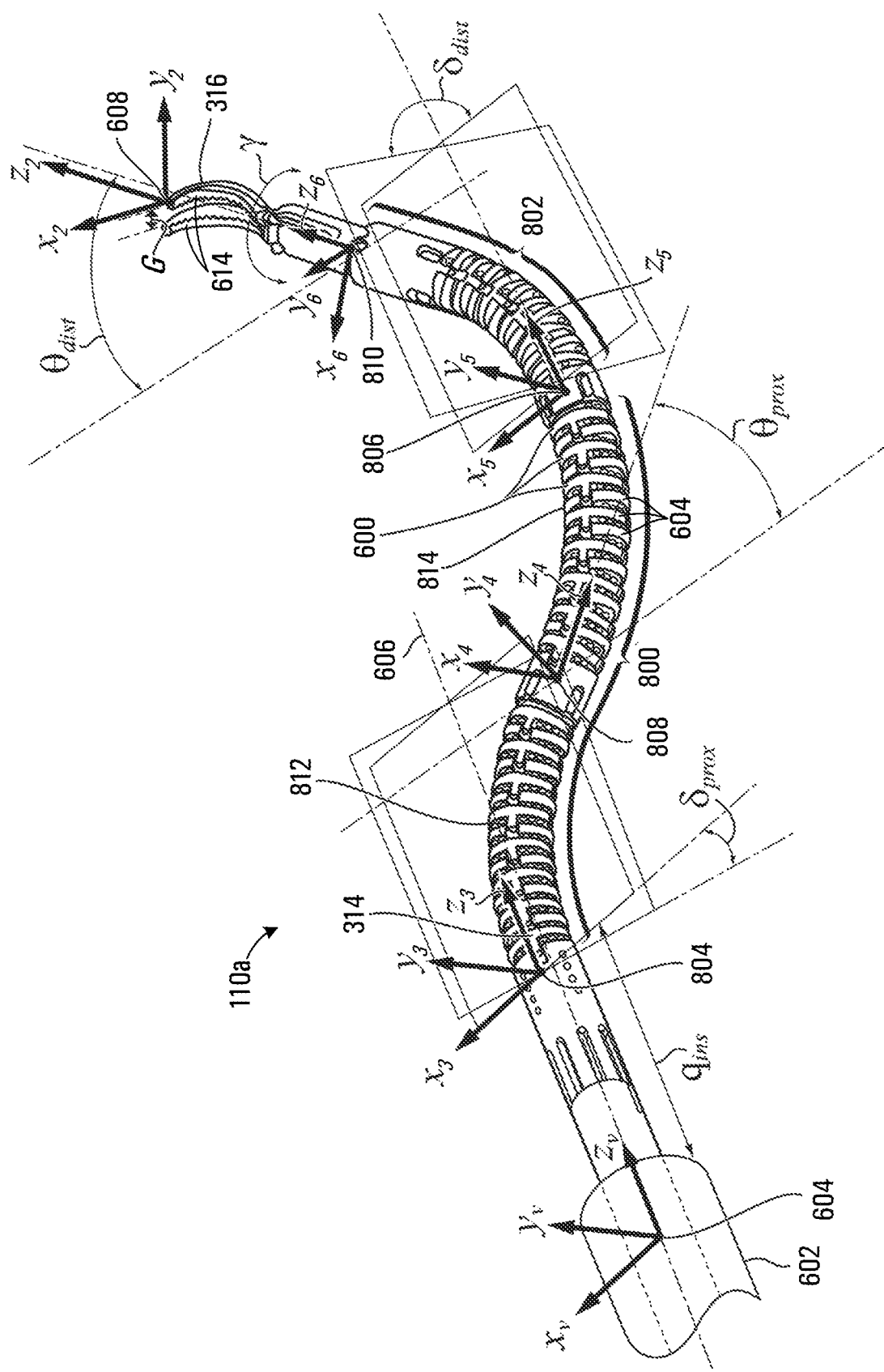
FIG. 8 is a perspective view of the right side instrument of FIG. 3B shown in a bent pose.
Figure 9:
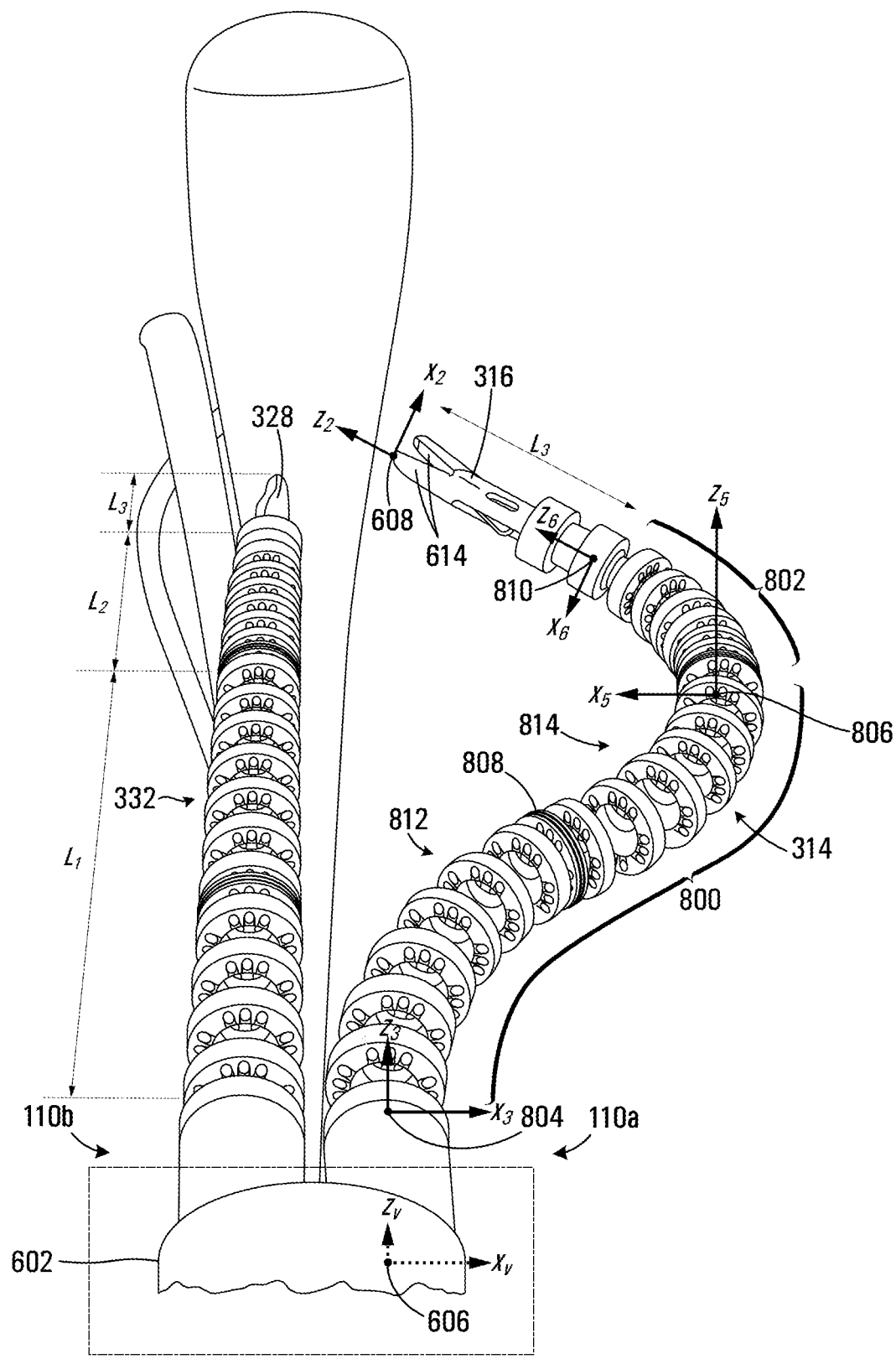
FIG. 9 is a rear perspective view of the right side instrument of FIG. 3B shown in a bent pose along with the left side instrument in a straight pose.

Generation of motion control signals (block 408, FIG. 4) by the instrument processor circuit 118 is described with further reference to FIG. 8 and FIG. 9. The right side instrument 110a is shown in FIG. 8 in a bent pose from a side perspective and from a rear perspective in FIG. 9. The left side instrument 110b is shown in FIG. 9 in a straight pose corresponding to the home configuration described above. Referring to FIG. 8 and FIG. 9, the positioner 314 of the instrument 110a has a first articulated segment referred to as an s-segment 800 and a second articulated segment referred to as a distal segment 802. The segments each include the plurality of vertebra 604. The s-segment 800 begins at a distance from the insertion tube 606, referred to as the insertion distance $q_{ins}$, which is a distance between the fixed responder reference position 608 defined at the origin of the responder fixed base reference frame $x_v$, $y_v$, and $z_v$ and a first position 804 at an origin of a first position reference frame $x_3$, $y_3$, and $z_3$. The insertion distance $q_{ins}$, represents an unbendable portion of the positioner 314 that extends out of the end of the insertion tube 606. In the embodiment shown, the insertion distance $q_{ins}$ may be about 10-20 mm, while in other embodiments the insertion distance may be longer or shorter, varying from 0-100 mm, for example.

The s-segment 800 extends from the first position 804 to a third position 806 defined as an origin of a third reference frame having axes $x_5$, $y_5$, and $z_5$ and is capable of assuming a smooth s-shape when control wires (not shown) inside the s-segment 800 are pushed and pulled by actuating the plurality of actuator slides 320 of the actuator 318 (FIG. 3B). The s-segment 800 has a mid-point at a second position 808, defined as the origin of a second position reference frame having axes $x_4$, $y_4$, and $z_4$. The s-segment 800 has a length $L_1$, best shown in FIG. 9 for the left side tool positioner 332 of the instrument 110b. In the embodiment shown, the length $L_1$ may be about 65 mm. The distal segment 802 extends from the third position 806 to a fourth position 810 defined as an origin of a fourth reference frame having axes $x_6$, $y_6$, and $z_6$. The distal segment 802 has a length $L_2$, best shown in FIG. 9 for the left side tool positioner 332. In the embodiment shown, the length $L_2$ may be about 30 mm.

Each end effector 316 and 334 also has an end effector length, which in the embodiment shown is a gripper length $L_3$ extending from the fourth position 810 to the end effector tip position 612 defined as the origin of the axes $x_2$, $y_2$, and $z_2$. The gripper length $L_3$ is best shown in FIG. 9 again for the left side tool positioner 332 and in one embodiment may be about 40 mm. The responder reference position 608, first position 804, second position 808, third position 806, fourth position 810, and the end effector position 612 may collectively be referred to as tool reference positions.

As described in PCT/CA2013/001076, by pushing and pulling on control wires inside the positioners 314 and 332, the s-segments 800 of the positioners may be bent into various degrees of an s-shape, from the straight condition shown in FIG. 6 to a partial or full s-shape for the right side instrument 110a shown in FIG. 8 and FIG. 9. The s-segment 800 is sectional in that it has a first section 812 and a second section 814 on opposite sides of the second position 808. Referring to FIG. 8, the first and second sections 812 and 814 lie in a first bend plane containing the first position 804, second position 808, and third position 806. The first bend plane is at an angle $\delta_{prox}$ to the $x_v$-$z_v$ plane of the fixed responder reference frame $x_v$, $y_v$, and $z_v$. The first section 812 and second section 814 are bent in the first bend plane through opposite but equal angles $\theta_{prox}$ such that no matter the angle $\theta_{prox}$ or the bend plane angle $\delta_{prox}$, the $z_5$ axis of the third position 806 is always parallel to and aligned in the same direction as the $z_v$ axis of the fixed responder reference position 608. Thus, by pushing and pulling on the control wires within the positioner 314, the third position 806 can be placed at any of a number of discrete positions in space within a cylindrical volume about the first position 804. This cylindrical volume may be referred to as the s-segment workspace.

In addition, the distal segment 802 lies in a second bend plane containing the third position 806 and the fourth position 810. The second bend plane is at an angle $\delta_{dist}$ to the $x_v$-$z_v$ plane of the fixed responder reference frame $x_v$, $y_v$, and $z_v$. The distal segment 802 is bent in the second bend plane at an angle $\theta_{dist}$. Thus, by pushing and pulling the control wires within the positioner 314, the fourth position 810 can be placed within another volume in space about the fourth position 810. This volume may be referred to as the distal workspace. The combination of the s-segment workspace and the distal workspace define the tool workspace 602 and represents the total possible movement of the positioner 314 of the instrument 110a as effected by the positioner 314. The left side instrument 110b may be similarly positioned by the positioner 332.

The distance between the fourth position 810 and the end effector position 612 is the distance between the movable portion of the distal segment 802 and the tip of the gripper 614 of the end effector 316 in the embodiment shown, i.e. the length the gripper length $L_3$ shown in FIG. 9. Generally, a portion of the gripper between the fourth position 810 and the end effector position 612 will be unbendable.

In the embodiment shown, the end effector 316 include moveable gripper jaws 614 that are rotatable about the $z_2$ axis in the $x_2$-$y_2$ plane of the end effector reference frame, the angle of rotation being represented by an angle γ relative to the positive $x_2$ axis. Finally, the gripper jaws 614 may be at any of varying degrees of openness from fully closed to fully open (as limited by a hinge joint of the jaws). The varying degrees of openness may be defined as "G". In summary therefore, the motion control signals are generated based on a kinematic configuration of the positioner 314 and end effector 316 as defined by the following configuration variables:

$q_{ins}$ represents a distance from the responder reference position 608 defined by axes $x_v$, $y_v$, and $z_v$ to the first position 804 defined by axes $x_3$, $y_3$ and $z_3$ where the s-segment 800 of the positioner 314 begins;

$\delta_{prox}$ represents a first bend plane in which the s-segment 800 is bent relative to the $x_v$-$y_v$ plane of the fixed responder reference frame;

$\theta_{prox}$ represents an angle at which the first and second sections 812 and 814 of the s-segment 800 are bent in the first bend plane;

$\delta_{dist}$ represents a second bend plane in which the distal segment 802 is bent relative to the $x_v$-$y_v$ plane of the fixed responder reference frame;

$\theta_{dist}$ represents an angle through which the distal segment 802 is bent in the second bend; γ represents a rotation of the end effector 316 about axis $z_2$; and G: represents a degree of openness of the gripper jaws 614 of the end effector 316 (this is a value which is calculated in direct proportion to a signal produced by an actuator (not shown) on the hand controller 122 indicative of an amount of pressure the operator exerts by squeezing the actuator to actuate the gripper jaws 614 to close).

To calculate the configuration variables, it will first be recalled that the end effector rotation matrix $R_{EENEW}$ is a 3×3 matrix:

$$R_{EENEW} = \begin{bmatrix} x_{2x} & y_{2x} & z_{2x} \\ x_{2y} & y_{2y} & z_{2y} \\ x_{2z} & y_{2z} & z_{2z} \end{bmatrix},$$

where the last column of $R_{EENEW}$ is the z-axis of the end effector reference frame written relative to the fixed responder reference frame $x_v$, $y_v$, and $z_v$. The values $\theta_{dist}$, $\delta_{dist}$, and γ associated with the distal segment 802 may be calculated according to the relations:

$$\theta_{dist} = \frac{\pi}{2} - \operatorname{atan2}\left(\sqrt{z_{2x}^2 + z_{2y}^2},\ z_{2z}\right) \quad \text{Eqn 2}$$

$$\delta_{dist} = -\operatorname{atan2}(z_{2y}, z_{2x}). \quad \text{Eqn 3}$$

If $|\delta_{dist}| > \frac{\pi}{2}$: Eqn 4a

γ = atan2(-$y_{2z}$, $x_{2z}$) - $\delta_{dist}$ + π else Eqn 4b

γ = atan2($y_{2z}$, -$x_{2z}$) - $\delta_{dist}$

The third position 806 may then be written in terms of a vector $\vec{p}_{3/v}$ from the fixed responder reference position 608 to the third position. Similarly, a vector $\vec{p}_{4/3}$ may be defined from the third position 806 to the fourth position 810 and a vector $\vec{p}_{5/4}$ may be defined from the fourth position 810 to the end effector position 612. These values can then be used to compute the location of third position 806 relative to the fixed responder reference position 608 by subtracting the vectors $\vec{p}_{4/3}$ and $\vec{p}_{5/4}$ from the end effector position vector $\vec{P}_{EENEW}$:

$$\vec{p}_{3/v} = \vec{P}_{EENEW} - \vec{p}_{4/3} - \vec{p}_{5/4}, \quad \text{Eqn 5}$$

where: Eqn 6a $$\vec{p}_{4/3} \cdot \vec{i} = \frac{-L_2 \cos\delta_{dist}(\sin\theta_{dist} - 1)}{\frac{\pi}{2} - \theta_{dist}}$$

$$\vec{p}_{4/3} \cdot \vec{j} = \frac{L_2 \sin\delta_{dist}(\sin\theta_{dist} - 1)}{\frac{\pi}{2} - \theta_{dist}} \quad \text{Eqn 6b}$$

$$\vec{p}_{4/3} \cdot \vec{k} = \frac{L_2 \cos(\theta_{dist})}{\frac{\pi}{2} - \theta_{dist}} \quad \text{Eqn 6c}$$

$$\vec{p}_{5/4} \cdot \vec{i} = L_3 \cos(\delta_{dist})\cos(\theta_{dist}) \quad \text{Eqn 7a}$$

$$\vec{p}_{5/4} \cdot \vec{j} = -L_3 \sin(\delta_{dist})\cos(\theta_{dist}) \quad \text{Eqn 7b}$$

$$\vec{p}_{5/4} \cdot \vec{k} = L_3 \sin(\theta_{dist}), \quad \text{Eqn 7c}$$

where $\vec{i}$ is a unit vector in the x direction, $\vec{j}$ is a unit vector in the y direction, and $\vec{k}$ is a unit vector in the z direction.

The vector $\vec{p}_{3/v}$ from the fixed responder reference position 608 to the third position 806 may then be used to find the configuration variables $\delta_{prox}$ and $\theta_{prox}$ for the s-segment 800. The angle $\delta_{prox}$ is calculated by solving the following two equations for $\delta_{prox}$:

$$\vec{p}_{3/v} \cdot \vec{i} = \frac{-L_1 \cos\delta_{prox}(\sin\theta_{prox} - 1)}{\frac{\pi}{2} - \theta_{prox}} \quad \text{Eqn 8a}$$

$$\vec{p}_{3/v} \cdot \vec{J} = \frac{L_1 \sin\delta_{prox}(\sin\theta_{prox} - 1)}{\frac{\pi}{2} - \theta_{prox}}. \quad \text{Eqn 8b}$$

Taking a ratio of Eqn 8b and Eqn 8a yields:

$$\delta_{prox} = a\tan 2(-\vec{p}_{3/v} \cdot \vec{j}, \vec{p}_{3/v} \cdot \vec{i}) \quad \text{Eqn 9}$$

where $\vec{i}$ and $\vec{j}$ are unit vectors in the x and y directions respectively. A closed form solution cannot be found for $\theta_{prox}$, and accordingly $\theta_{prox}$ must be found using a numerical equation solution to either of equations Eqn 8a or Eqn 8b. For example, a Newton-Raphson method may be employed, which iteratively approximates successively better roots of a real-valued function. The Newton-Raphson method can be implemented using the following equations:

$$f(\theta_{prox}) = \frac{L_1}{\frac{\pi}{2} - \theta_{prox}} \cos\delta_{prox}(1 - \sin\theta_{prox}) - \vec{p}_{3/v} \cdot \vec{i} = 0, \quad \text{Eqn 10}$$

where $\vec{i}$ is the unit vector in the x direction. The equation Eqn 10 is Eqn 8a rewritten in the form $f(\theta_{prox})=0$. The Newton-Raphson method tends to converge very quickly because in the range $0<\theta_{prox}<\pi$, the function has a large radius of curvature and has no local stationary points. Following the Newton-Raphson method, successive improved estimates of $\theta_{prox}$ can be made iteratively to satisfy equation Eqn 10 using the following relationship:

$$\theta_{n+1} = \theta_n - \frac{f(\theta_n)}{f'(\theta_n)} \qquad \text{Eqn 11}$$

Finally, upon determination of $\theta_{prox}$, the following equation can be used to find $q_{ins}$:

$$q_{ins} = -\bar{p}_{3/v} \cdot \bar{k} - \frac{L_1 \cos\theta_{prox}}{\frac{\pi}{2} - \theta_{prox}}, \qquad \text{Eqn 12}$$

where $\bar{k}$ is the unit vector in the z direction and $\bar{p}_{3/v} \cdot \bar{k}$ is the dot product of the vector $\bar{p}_{3/v}$ and the unit vector $\bar{k}$.

The above configuration variables are calculated for the end effector position and orientation signals $\vec{P}_{EENEW}$ and $R_{EENEW}$ at block 706 or $\vec{P}_{EEPREV}$ and $R_{EEPREV}$ at block 714 of the processes 700. The configuration variables generally define a pose of the positioner 314 required to position the end effector 316 at the desired location and orientation in end effector workspace. Configuration variables are produced for each end effector 316 and 334 of the respective right and left side instruments 110a and 110b. Two sets of configuration variables referred to as right and left configuration variables respectively are thus produced and transmitted by the motion control interface 408 to the instrument processor circuit 118 and used by the microprocessor 280 to generate drive control signals for spatially positioning the positioner 314 and end effector 316 of the instrument 110a in the surgical workspace 600.

The values of the vector $\vec{P}_{EENEW}$ and rotation matrix $R_{EENEW}$ calculated as described above and stored in stores 430 and 432 of the current buffer 420 of the workstation memory 402 thus define the location (x, y, z) of the end effector 316 of the instrument 110a within the surgical workspace 600 relative to the fixed responder reference frame $x_v$, $y_v$, $z_v$ (shown in FIG. 6).

Figure 10:
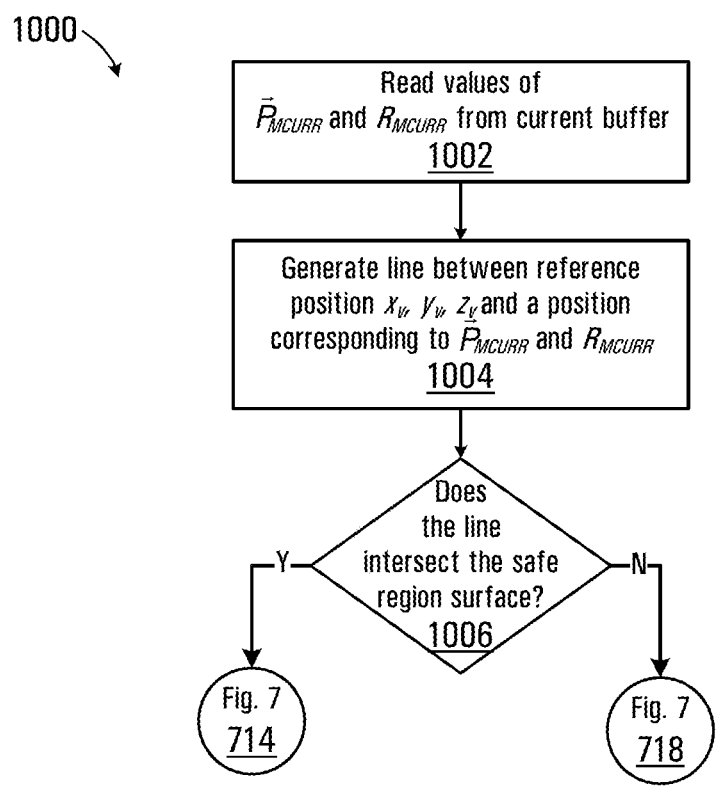
FIG. 10 is a flowchart of a process implemented by the workstation processor circuit of FIG. 4 for making a determination as to whether a desired spatial positioning of the end effector is associated with a service life reduction.

Referring to FIG. 10, a process for implementing block 712 of the movement process 700 (FIG. 7) is shown generally at 1000. The process 1000 causes the microprocessor 400 to make the determination as to whether the desired spatial positioning of the end effector 316 by the tool positioner 314 is associated with a service life reduction. Block 1002 directs the microprocessor 400 to read the values of the vector $\vec{P}_{MCURR}$ and rotation matrix $R_{MCURR}$ from the stores 422 and 424 of the current buffer 420. Block 1004 then directs the microprocessor 400 to generate a notional line extending from the reference position 618 $x_s$, $y_s$, $z_s$ (in FIG. 6) to the position defined by the values of $\vec{P}_{MCURR}$ and $R_{MCURR}$. Block 1006 then directs the microprocessor 400 to determine whether the generated line intersects the save region surface 616. If at block 1006, the line intersects the surface 616, then the end effector position 612 corresponding to $\vec{P}_{MCURR}$ and $R_{MCURR}$ would be outside the safe region 616 and would thus potentially result in a reduction in service life for the tool positioner 314 of the instrument 110. Block 1006 then directs the microprocessor 400 to block 718 of the process 700 for initiation of the movement management function.

If at block 1006, the notional line does not intersect the surface 616, then the end effector position 612 corresponding to $\vec{P}_{MCURR}$ and $R_{MCURR}$ would be within the safe region 616 and would thus not result in a reduction in service life for the tool positioner 314 of the instrument 110. Block 1006 then directs the microprocessor 400 to block 714 of the process 700 and motion control signals are transmitted to the instrument processor circuit 118 to facilitate movement of the end effector 316.

In the process 1000 the vector $\vec{P}_{MCURR}$ and rotational matrix $R_{MCURR}$ represent desired positions for the end effector 316 of the instrument 110a. However physical movement of the tool positioner 314 only occurs after the workstation processor circuit 114 writes these values to the values the vector $\vec{P}_{EENEW}$ and rotation matrix $R_{EENEW}$ stored in stores 430 and 432 of the current buffer 420 and then transmits these values via the interface cable 116 to the instrument processor circuit 118.

Figure 11A:
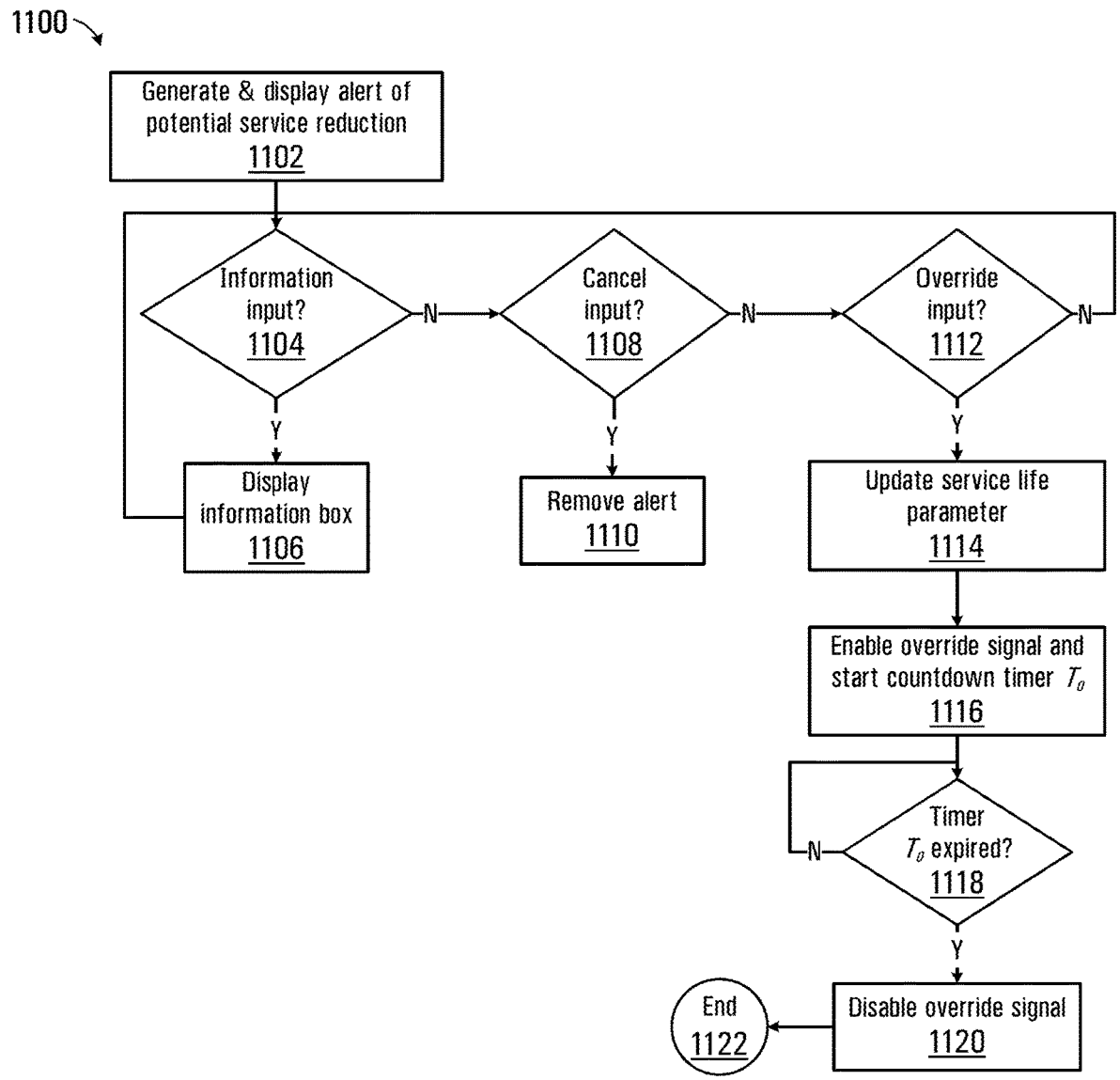
FIG. 11A is a flowchart of a movement management process implemented by the workstation processor circuit shown in FIG. 4.
Figure 11B:
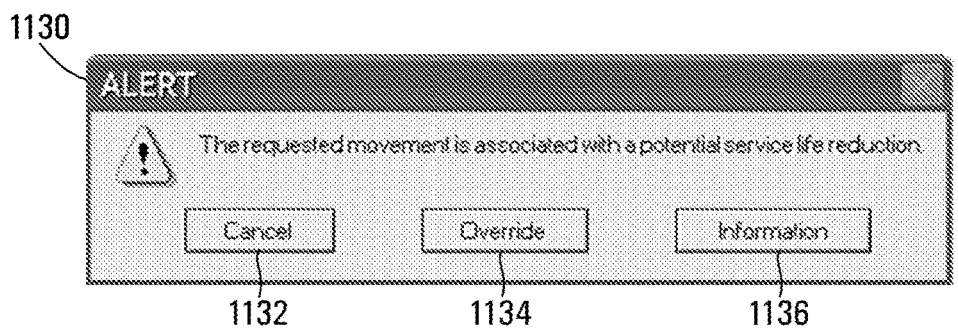
FIG. 11B is a screenshot of an example alert displayed during the process of FIG. 11A.

Referring to FIG. 11A, an embodiment of a movement management process for implementing block 718 of the movement process 700 is shown generally at 1100. The movement management process 1100 runs in parallel with the movement process 700 and begins at block 1102. Block 1102 directs the microprocessor 400 to generate an alert that the movement to the desired spatial position is associated with a potential service reduction. An example of a displayed alert is shown in FIG. 11B at 1130. The alert 1130 includes a message indicating that the requested movement is associated with a potential service life reduction and provides a "Cancel" button 1132, an "Override" button 1134, and an "Information" button 1136, for receiving an operator selection. The alert 1130 may be displayed on the display 120 and/or on the secondary display 132. Block 1102 then directs the microprocessor 400 to block 1104, which directs the microprocessor 400 to determine whether the "Information" button 1136 has been activated by the operator. If the information button 1136 has been selected the process continues at block 1106, which directs the microprocessor 400 to display additional information. For example, a pop-up box (not shown) may be displayed on the display 120 or secondary display 132 that includes information such as the current remaining service life for the instrument, background information on the reasons for the movement causing a service life reduction, and information on the override process. The Information display may include a cancel button for returning to the displayed alert 1130 once the operator has reviewed the information presented. Block 1106 then directs the microprocessor 400 back to block 1104.

If at block 1104, the "Information" button 1136 was not activated, the microprocessor 400 is directed to block 1108. Block 1108 directs the microprocessor 400 to determine whether the "Cancel" button 1132 has been activated by the operator. If the "Cancel" button 1132 was activated, the microprocessor 400 is directed to block 1110, which directs the microprocessor 400 to discontinue display of the alert 1130. The movement process 700 continues to run as before and if the operator still provides input via the input device 112 that represent a desired end effector position outsider the safe region 616, block 712 will again direct the microprocessor 400 to block 718 and the process 1100 will be re-initiated and the alert 1130 will be displayed again.

If at block 1108, the "Cancel" button 1132 was not activated, the microprocessor 400 is directed to block 1112, which directs the microprocessor 400 to determine whether the "Override" button 1134 has been activated by the operator. If the "Override" button 1134 has not been activated, the microprocessor 400 is directed back to block 1104, which causes blocks 1104, 1108, and 1112 to be repeated until the operator makes a selection of one of the buttons 1132, 1134, or 1136. If at block 1112, the "Override" button 1134 has been activated, the microprocessor 400 is directed to block 1114. Block 1114 directs the microprocessor 400 to update a service life parameter for the instrument 110a. In the embodiment shown in FIG. 4, the service life parameter of the instrument 110a is stored in the memory 464 on the monitor board 328. The memory 464 of the monitor board 328 may be accessed by the instrument processor circuit 118 via the instrument interface 458 and interface 462 on the monitor board. In one embodiment the microprocessor 400 may send an update command via the interface cable 116 that causes the microprocessor 450 of the instrument processor circuit 118 to initiate the necessary update to the service life parameter.

In some embodiments, the instrument 110a when newly manufactured may have a pre-determined number of uses loaded into the memory 464 on the monitor board 328. As an example, an instrument may be designed to be reused a number of times (for example 20 times). During each use, the mechanical structures of the instrument 110a will be subjected to some stresses and eventually components of the instrument may become strained or worn. Additionally, following each use the instrument 110a must be cleaned and sterilized, which may involve autoclaving or other processes that cause additional stress and/or deterioration of the materials and components of the instrument. The determination that a desired spatial positioning would result in a movement of the positioner 314 associated with a potential service life reduction may be based on an estimated strain in the control wires associated with the movement. Positions within the tool workspace 602 that are associated with increased strain in the control wires may be mapped to generate the safe region 616 as shown in FIG. 6.

In this embodiment, the service life parameters are stored in the memory 464 rather than the workstation processor circuit 114 or instrument processor circuit 118. This avoids circumvention of the service life restrictions by simply using the instrument with another system 100. The interface 462 may also implement security functions for controlling access for reading and writing to the memory 464. The security functions may be implemented to prevent unauthorized access to the memory 464 for changing the remaining service life of the instrument 110a. As an example, the interface 462 may implement a cryptography system that uses pairs of cryptographic keys to prevent access to the memory 464 by a host not having a corresponding cryptographic key. In other embodiments, although less desirable, the service life parameter may be stored in the workstation memory 402 or the memory 452 of the instrument processor circuit 118.

Use of the instrument 110a outside the safe region 616 shown in FIG. 6 results in additional strain in the control wires and may cause additional wear of the vertebra 604. The updating of the service life parameter accounts for this additional strain by reducing the number of service lives remaining for the instrument. For example, a single override may be associated with a reduction of one or more of the 20 uses, as set out in the example above.

Once the service life parameter has been updated at block 1114, the microprocessor 400 is directed to block 1116. Block 1116 directs the microprocessor 400 to enable or assert the override signal for use at block 720 of the movement process 700, as described above. Block 1116 also directs the microprocessor 400 to start a countdown timer $T_o$. The countdown timer provides a pre-determined override period during which the operator is able to provide inputs to the input device 112 that cause the end effector to be positioned outside of the safe region 616. For example, the timer $T_o$ may be set for 30 or 60 seconds. The microprocessor 400 is then directed to block 1118, which directs the microprocessor to determine whether the countdown timer To has expired. If the timer has not yet expired, block 1118 is repeated. If at block 1118, the timer $T_o$ has expired, the microprocessor 400 is directed to block 1120. Block 1120 directs the microprocessor 400 to disable the override signal. As such, the microprocessor 400 will discontinue transmitting drive signals at block 714 of the movement process 700 for movements of the positioner 314 that are associated with the potential service life reduction on expiry of an override period. Block 1120 then directs the to block 1122, where the movement management process 1100 ends. A further determination at block 712 as to whether the desired spatial positioning of the end effector 316 is outside the safe region 616 may again trigger the movement management process 1100.

In an alternative embodiment, the service life parameter may correspond to a pre-determined usage time for the instrument 110a. In this case the microprocessor 400 may be configured to decrement a usage time parameter stored in the memory 464 of the monitor board 328 based on an expected reduction in service life-time caused by the movement. Various other alternatives for implementing the service life parameter may include a parameter that includes a pre-determined number of movements of the positioner 314 of the instrument 110a associated with a potential service life reduction. For example, it may be pre-determined that the instrument 110a can safely move outside the safe region 616 a certain number of times and the microprocessor 400 may be configured to decrement a remaining number of these movements stored in the memory 464 of the monitor board 328 each time the override input is received from the operator.

Referring back to FIG. 1, in the embodiment shown an image of the surgical workspace including anatomical features and the instruments 110 is displayed on the display 120. In one embodiment the movement management block 718, when initiated causes an alert icon 130 to be displayed overlaying a portion of an image of the left hand side tool. In other embodiments the alert may take the form of causing a portion of the screen such as the screen border to be colored red or by causing the screen to flash.

Alternatively, the workstation 102 may include an audible warning device that is capable of generating an alert tone. The alert tone may be combined with a display of the alert 1130 in FIG. 11B on the secondary display 132.

As disclosed above, the input device 112 may be configured to generate haptic forces for providing feedback to the operator via to the hand controllers 122 and 124. In one embodiment the alert may involve the movement management block 718 directing the microprocessor 400 to generate a haptic feedback signal that is communicated to the input device 112 via the USB connection 518 to cause generation of haptic forces. As an example, when the left hand instrument 110 generates input signals that would result in the end effector of the right hand instrument 110a moving outside of the safe region 616, then the right hand controller 122 may generate a perceptible force on the hand controller 122 that provides the alert to the operator while grasping the hand controller.

Figure 12:
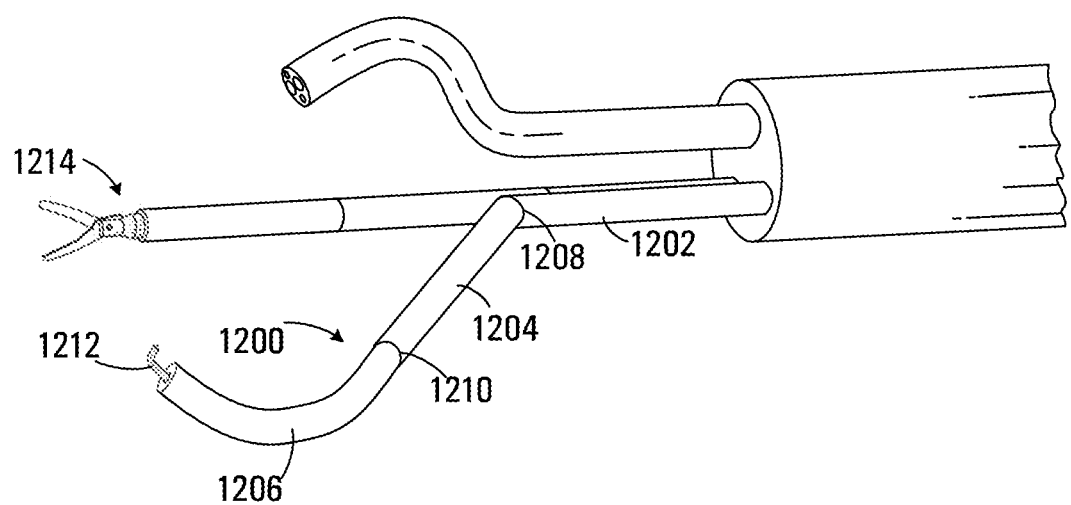
FIG. 12 is a perspective view of an instrument including an alternative positioner.

The instrument 110a in the embodiment described above includes articulated linkages in the form of vertebra 604 that provide smoothly bendable articulated segments sections 800 and 802 shown in FIG. 9. Referring to FIG. 12, in another embodiment an instrument 1200 includes linkages 1202 and 1204 and a wrist 1206 that are articulated at discrete joints 1208 and 1210. The articulated linkages 1202 and 1204 include control wires (not shown) that run through the linkages and activate the instrument 1200 to cause bending at the discrete joints 1208 and 1210. In this embodiment the wrist 1206 includes articulated segments as generally described above that provide a smoothly bendable linkage for positioning an end effector 1212 in a surgical workspace. A second instrument 1214 is similarly configured. The above described embodiments may be implemented for the instruments 1200 and 1214.

While the above embodiments have been described in terms of a positioning function, the process may be implemented for mechanical functions other than positioning. For example, referring back to FIG. 8, the gripper jaws 614 pf the end effector 316 may be actuated to open and close by one of the actuator slides 320. The applicable actuator slide 320 thus provides an actuation force by tensioning control wires extending along the positioner 314 and coupled to one or both of the gripper jaws 614 of the end effector 316 at the distal end of the positioner. The microprocessor 400 of the workstation processor circuit 114 may be configured to generate end effector drive signals for causing the opposing gripper jaw elements to close with a desired force in proportion to an end effector actuation signal. The actuation signal is generated by the input device 112 in response to a force imparted by the operator on the end effector actuator 520 of the input device 112 shown in FIG. 5. The end effector actuator 520 may provide a force sensitive input that generates end effector input signals in response to a force exerted by the operator on the actuator. The microprocessor 400 may be configured to make a determination that the desired force would result in a potential service life reduction for the actuation of the gripper jaws 614. As described above, the microprocessor 400 may initiate an actuation management function. Similarly, if the microprocessor 400 determines that the desired force would not result in a potential service life reduction for the instrument, end effector drive signals may be generated to cause the end effector to close with the desired force.

There is provided a non-transitory computer readable medium storing instructions, which when executed by at least one processor, cause the at least one processor to perform any of the methods as generally shown or described herein and equivalents thereof.

While specific embodiments have been described and illustrated, such embodiments should be considered illustrative only and not as limiting the disclosed embodiments as construed in accordance with the accompanying claims.

What is claimed is:

1. A robotic surgery system comprising:
    an input device configured to generate an input signal in response to manipulation by an operator; and
    a processor configured to:
        receive the input signal from the input device;
        process the input signal to determine a desired spatial positioning of an instrument within an instrument workspace;
        provide an indication in response to a determination that the desired spatial positioning would result in a movement associated with a potential service life reduction of the instrument; and
        in response to a determination that the desired spatial positioning would not result in the movement associated with the potential service life reduction of the instrument, cause the instrument to be positioned at the desired spatial positioning in the instrument workspace.

2. The system of claim 1 wherein the processor is configured to make the determination that the desired spatial positioning would result in the movement associated with the potential service life reduction by determining that the desired spatial positioning associated with the input signal lies outside a pre-determined safe region of the instrument workspace.

3. The system of claim 2, wherein the processor is configured to initiate a movement management function by temporarily permitting the operator to extend the pre-determined safe region to permit the instrument to move outside the pre-determined safe region.

4. The system of claim 1 wherein the processor is configured to initiate a movement management function by:
    causing an alert to be generated to indicate to the operator that the movement is associated with the potential service life reduction; and
    causing the instrument to remain positioned at a current position in the instrument workspace.

5. The system of claim 4 wherein the input device is configured to deliver a haptic feedback to an operator of the input device, and wherein the processor is configured to generate the alert by causing the input device to deliver the haptic feedback.

6. The system of claim 1 wherein the processor is configured to initiate a movement management function by:
    causing an alert to be generated to indicate to the operator that the desired spatial positioning is associated with the potential service life reduction; and
    in response to receiving an override input from the operator:
        causing the instrument to be positioned at the desired spatial positioning in the instrument workspace; and
        update a service life parameter associated with the instrument based on an expected reduction in service life caused by the movement.

7. The system of claim 6 wherein the service life parameter comprises a pre-determined number of uses for the instrument, the pre-determined number of uses being decremented each time the instrument is used in a surgical procedure, and wherein the processor is configured to decrement the pre-determined number of uses based on the expected reduction in service life caused by the movement.

8. The system of claim 6 wherein the service life parameter comprises a pre-determined usage time, and wherein the processor is configured to decrement the pre-determined usage time based on the expected reduction in service life caused by the movement.

9. The system of claim 6 wherein the service life parameter comprises a pre-determined number of movements associated with the potential service life reduction, and wherein the processor is configured to decrement the pre-determined number of movements each time the override input is received from the operator.

10. The system of claim 6 wherein the processor is configured to discontinue causing the instrument to be positioned at the desired spatial positioning associated with the potential service life reduction responsive to expiry of an override period.

11. The system of claim 6 further comprising a display configured to display an image of the instrument workspace to the operator, and wherein the processor is configured to cause the alert to be generated by causing displaying of an alert icon on the display.

12. The system of claim 11 wherein the processor is configured to cause displaying an interactive alert icon on the display, the interactive alert icon being configured to generate the override input when activated by the operator.

13. The system of claim 6 wherein the input device is configured to deliver a haptic feedback to an operator of the input device, and wherein the processor is configured to generate the alert by causing the input device to deliver the haptic feedback.

14. The system of claim 1 wherein a service life parameter is configured to be stored in a memory associated with the instrument, and wherein the processor is configured to update the service life parameter by writing a new service life parameter to the memory.

15. The system of claim 14 wherein the memory comprises a memory located on the instrument, and wherein the system comprises an instrument interface configured to place the processor in data communication with the memory responsive to the instrument being loaded into the system.

16. The system of claim 15 wherein access for reading and writing to the memory is protected by a security function to prevent unauthorized changes to the service life parameter.

17. The system of claim 14 wherein the memory comprises a memory of the processor, and wherein the service life parameter includes an identifier that associates the service life parameter with the instrument.

18. The system of claim 1 wherein a positioner of the instrument comprises:
  a plurality of articulated linkages; and
  a plurality of control wires that are pushed or pulled to cause movement of the plurality of articulated linkages to position the instrument within the instrument workspace;
  wherein the determination that the desired spatial positioning would result in the movement associated with the potential service life reduction is based on an estimated strain in the plurality of control wires associated with the movement.

19. The system of claim 1 wherein the instrument comprises an end effector positioned at a distal end of the instrument, and wherein the end effector comprises a pair of opposing elements, the opposing elements being actuated to close by an end effector actuation signal received from the input device, and wherein the processor is configured to:
  determine an end effector drive signal for causing the opposing elements to close with a desired force in proportion to the end effector actuation signal;
  provide an indication in response to a determination that the desired force would result in the potential service life reduction of the instrument; and
  in response to a determination that the desired force would not result in the potential service life reduction of the instrument, cause the end effector to close with the desired force.

20. A method for operating a robotic surgery system, the robotic surgery system including a processor and an input device, the method comprising by the processor:
  receiving an input signal in response to manipulation of the input device by an operator;
  processing the input signal to determine a desired spatial positioning of an instrument within an instrument workspace;
  providing an indication in response to a determination that the desired spatial positioning would result in a movement associated with a potential service life reduction of the instrument; and
  in response to a determination that the desired spatial positioning would not result in a movement associated with the potential service life reduction of the instrument, causing the instrument to be positioned at the desired spatial positioning in the instrument workspace.

21. The method of claim 20 further comprising initiating an movement management function comprises:
  generating an alert to indicate to the operator that the desired spatial positioning is associated with the potential service life reduction; and
  in response to receiving an override input from the operator:
    causing the instrument to be positioned at the desired spatial positioning in the instrument workspace; and
    updating a service life parameter associated with the instrument based on an expected reduction in service life.

* * * * *